(12) United States Patent
Ogilvie et al.

(10) Patent No.: US 6,716,836 B2
(45) Date of Patent: Apr. 6, 2004

(54) NON-NUCLEOSIDE REVERSE TRANSCRIPTASE INHIBITORS

(75) Inventors: William W. Ogilvie, Ottawa (CA); Robert Déziel, Mont-Royal (CA); Julie Naud, Boisbriand (CA); Jeffrey O'Meara, Boisbriand (CA); Dale R. Cameron, Richmond (CA)

(73) Assignee: Boehringer Ingelheim (Canada) Ltd., Laval (CA)

( * ) Notice: Subject to any disclaimer, the term of this patent is extended or adjusted under 35 U.S.C. 154(b) by 63 days.

(21) Appl. No.: 10/096,779

(22) Filed: Mar. 13, 2002

(65) Prior Publication Data
US 2003/0069226 A1 Apr. 10, 2003

Related U.S. Application Data
(60) Provisional application No. 60/278,044, filed on Mar. 22, 2001.

(51) Int. Cl.[7] .................. A61K 31/55; C07D 471/14
(52) U.S. Cl. .................. 514/220; 514/183; 540/495
(58) Field of Search .................. 514/183, 220; 540/495

(56) References Cited

U.S. PATENT DOCUMENTS

| 5,366,972 A | | 11/1994 | Hargrave et al. ........... 514/220 |
| 5,620,974 A | * | 4/1997 | Hargrave et al. ........... 514/220 |
| 5,705,499 A | | 1/1998 | Cywin et al. ............... 514/220 |

FOREIGN PATENT DOCUMENTS

WO   WO 01/96338 A1   12/2001

OTHER PUBLICATIONS

U.S. patent application Ser. No. 10/205,094, Oglivie et al., filed Jul. 2002.*
U.S. patent application Ser. No. 60/367,971, O'meara et al., filed Mar. 2002.*
Hargrave, et al; "Novel Non-Nucleoside Inhibitors of HIV-1 Reverse Transcriptase. 1. Tricyclic Pyridobenzo- and Dipyridodiazepinones"; J. Med. Chem. 1991, 34, 2231–2241.
Cywin, et al.; "Novel Nonnucleoside Inhibitors of HIV-1 Reverse Transcriptase. 8. 8-Aryloxymethyl- and 8-Arylthiomethyldipyridodiazepinones1"; J. Med. Chem. 1998, 41, 2972–2984.
Klunder, et al; "Novel Nonnucleoside Inhibitors of HIV-1 Reverse Transcriptase. 7. 8-Arylethyldipyridodiazepinones as Potent Broad-Spectrum Inhibitors of Wild-Type and Mutant Enzymes"; J. Med. Chem. 1998, 41, 2960–2971.
Lombardino; "Preparation of Substituted 1,2-Benzxoisothiazolin-3-one 1,1-Dioxides (o-Benzoic Sulfimides)"; J. Org. Chem., vol. 36, No. 13, 1971, 1843–1845.
Blondet, et al; "A Convenient Synthesis of 3,4-Dihydro-2, 2-Dioxide 5-Hydroxy-2,1-Benzothiazine"; Tetrahedron Letters, vol. 35, No. 18, 2911–2912, 1994.

* cited by examiner

Primary Examiner—Mukund J. Shah
Assistant Examiner—Sudhaker B. Patel
(74) Attorney, Agent, or Firm—Robert P. Raymond; Alan R. Stempel; Mary-Ellen M. Devlin

(57) ABSTRACT

A compound of formula I:

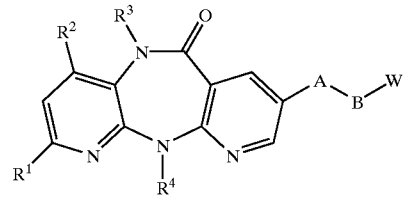

wherein
A is a connecting chain of $(C_{1-3})$ alkyl; B is O or S; $R^1$ is H, $(C_{1-6})$ alkyl, halo, $CF_3$, or $OR^{1a}$ wherein $R^{1a}$ is H or $(C_{1-6})$alkyl; $R^2$ is H or Me; $R^3$ is H or Me; $R^4$ is H, $(C_{1-4})$ alkyl, $(C_{3-4})$ cycloalkyl and $(C_{1-4})$alkyl$(C_{3-7})$ cycloalkyl;
W is selected from

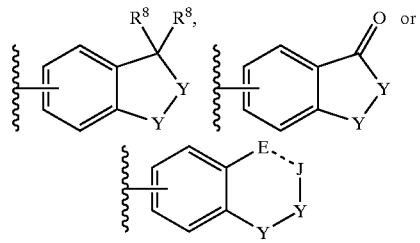

wherein,
a) one of Y is $SO_2$ and the other Y is $NR^5$, provided that both are not the same, wherein $R^5$ is H, $(C_{1-6})$alkyl, $(C_{3-6})$ cycloalkyl, the alkyl being substituted, $COR^{5o}$, $COOR^{5p}$ or $CONR^{5p}PR^{5q}$; and each $R^8$ is H, $(C_{1-4})$ alkyl, $(C_{3-6})$ cycloalkyl, or $(C_{1-4})$ alkyl-$(C_{3-6})$ cycloalkyl; or b) E is $CR^{8a}R^{8b}$ wherein $R^{8a}$ and $R^{8b}$ is H, or alkyl and J is $CH_2$; or J is $CR^{8a}R^{8b}$ and E is $CH_2$, and the dotted line represents a single bond; or c) E is C(O) and J is $CR^{8a}R^{8b}$ or J is C(O) and E is $CR^{8a}R^{8b}$ and the dotted line represents a single bond; or d) E and J are $CR^{8a}R^{8b}$ and the dotted line represents a double bond. Compounds of formula I have activity against HIV WT and double mutant strains.

62 Claims, No Drawings

NON-NUCLEOSIDE REVERSE TRANSCRIPTASE INHIBITORS

RELATED APPLICATIONS

Benefit of U.S. Provisional Application Serial No. 60/278,044, filed on Mar. 22, 2001 is hereby claimed.

TECHNICAL FIELD OF THE INVENTION

The invention relates to novel compounds and pharmaceutically acceptable salts thereof, their use, either alone or in combination with other therapeutic agents, in the treatment or prophylaxis of HIV infection, and to pharmaceutical compositions comprising the compounds that are active against NNRTI resistant mutants.

BACKGROUND OF THE INVENTION

The disease known as acquired immune deficiency syndrome (AIDS) is caused by the human immunodeficiency virus (HIV), particularly the strain known as HIV-1. In order for HIV to be replicated by a host cell, the information of the viral genome must be integrated into the host cell's DNA. However, HIV is a retrovirus, meaning that its genetic information is in the form of RNA. The HIV replication cycle therefore requires a step of transcription of the viral genome (RNA) into DNA, which is the reverse of the normal chain of events. An enzyme that has been aptly dubbed reverse transcriptase (RT) accomplishes the transcription of the viral RNA into DNA. The HIV virion includes a copy of RT along with the viral RNA.

Reverse transcriptase has three known enzymatic functions; it acts as an RNA-dependent DNA polymerase, as a ribonuclease, and as a DNA-dependent DNA polymerase. Acting as an RNA-dependent DNA polymerase, RT transcribes a single-stranded DNA copy of the viral RNA. Acting as a ribonuclease, RT destroys the original viral RNA, and frees the DNA just produced from the original RNA. Finally, acting as a DNA-dependent DNA polymerase, RT makes a second, complementary DNA strand, using the first DNA strand as a template. The two strands form double-stranded DNA, which is integrated into the host cell's genome by another enzyme called integrase.

Compounds that inhibit the enzymatic functions of HIV-1 reverse transcriptase will inhibit replication of HIV-1 in infected cells. Such compounds are useful in the prevention or treatment of HIV-1 infection in human subjects, as demonstrated by known RT inhibitors such as 3'-azido-3'-deoxythymidine (AZT), 2',3'-dideoxyinosine (ddI), 2',3'-dideoxycytidine (ddC), d4T, 3TC, Nevirapine, Delavirdine, Efavirenz and Abacavir, the main drugs thus far approved for use in the treatment of AIDS.

As with any antiviral therapy, use of RT inhibitors in the treatment of AIDS eventually leads to a virus that is less sensitive to the given drug. Resistance (reduced sensitivity) to these drugs is the result of mutations that occur in the reverse transcriptase segment of the pol gene. Several mutant strains of HIV have been characterised, and resistance to known therapeutic agents is believed to be due to mutations in the RT gene. One of the more commonly observed mutants clinically, is the Y181 C mutant, in which a tyrosine (Y), at codon 181, has been mutated to a cysteine (C) residue. Other mutants, which emerge with increasing frequency during treatment using known antivirals, include single mutants K103N, V106A, G190A, Y188C, and P236L, and double mutants K103N/Y181C, K103N/P225H, K103N/N108I and K103N/L100I.

As antiviral use in therapy and prevention of HIV infection continues, the emergence of new resistant strains is expected to increase. There is therefore an ongoing need for new inhibitors of RT, which have different patterns of effectiveness against the various resistant mutants.

Compounds having tricyclic structures, which are inhibitors of HIV-1, are described in U.S. Pat. No. 5,366,972. Other inhibitors of HIV-1 reverse transcriptase are described in Hargrave et al., J. Med Chem., 34, 2231 (1991), Cywin et al., J. Med. Chem., 41, 2972 (1998) and Klunder et al., J. Med. Chem., 41, 2960 (1998).

U.S. Pat. No. 5,705,499 proposes 8-arylalkyl- and 8-arylhetroalkyl-5,11-dihydro-6H-dipyrido[3,2-B:2',3'-E][1,4]diazepines as inhibitors of RT. The exemplified compounds are shown to have some activity against HIV WT reverse transcriptase.

WO 01/96338A1 discloses diazepine structures having quinoline and quinoline-N-oxide substituents as inhibitors of RT. The exemplified compounds have activity against HIV WT, single and double mutant strains.

SUMMARY OF THE INVENTION

The invention provides novel sultam-containing compounds that are potent inhibitors of wild-type (WT) and double mutant strains of HIV-1 RT, particularly the double mutation K103N/Y181C.

According to a first aspect of the invention, there is provided a compound of formula I:

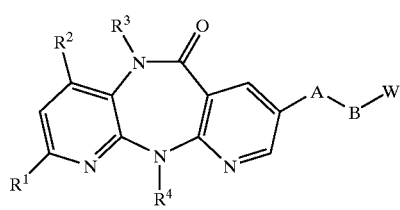

wherein
A is a connecting chain of $(C_{1-3})$ alkyl;
B is O or S;
$R^1$ is H, $(C_{1-6})$alkyl, halo, $CF_3$, or $OR^{1a}$ wherein $R^{1a}$ is H or $(C_{1-6})$alkyl;
$R^2$ is H or Me;
$R^3$ is H or Me;
$R^4$ is selected from the group consisting of: H, $(C_{1-4})$ alkyl, $(C_{3-4})$ cycloalkyl and $(C_{1-4})$alkyl-$(C_{3-4})$ cycloalkyl;
W is selected from

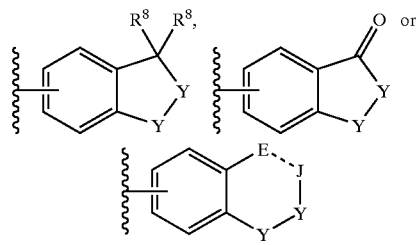

wherein,
a) one of Y is $SO_2$ and the other Y is $NR^5$, provided that both are not the same, wherein $R^5$ is selected from the group consisting of: H, $(C_{1-6})$alkyl, $(C_{3-6})$ cycloalkyl, said alkyl being optionally substituted with a substituent selected from the group consisting of:
  (i) ($C_{3-6}$ cycloalkyl);
  (ii) 5- or 6-membered heterocycle having 1 to 4 heteroatom selected from O, N, and S, said heterocycle being optionally substituted with ($C_{1-6}$) alkyl;
  (iii) $NR^{5a}R^{5b}$, wherein $R^{5a}$ and $R^{5b}$ is both H or ($C_{1-6}$)alkyl said alkyl being optionally substituted with ($C_{1-6}$)alkoxy, ($C_{6-10}$)aryl or 5- or 6-membered heterocycle having 1 to 4 heteroatom selected from O, N, and S, said heterocycle being optionally mono- or di-substituted with ($C_{1-6}$) alkyl;
  (iv) $OR^{5c}$ wherein $R^{5c}$ is H, ($C_{1-6}$) alkyl or 5- or 6-membered heterocycle having 1 to 4 heteroatom selected from O, N, and S;
  (v) $OCONR^{5d}R^{5e}$, wherein $R^{5d}$ and $R^{5e}$ are both H; or $R^{5d}$ is H and $R^{5e}$ is ($C_{1-6}$)alkyl;
  (vi) $COOR^{5f}$, wherein $R^{5f}$ is H or ($C_{1-6}$)alkyl;
  (vii) $CONR^{5g}R^{5h}$ wherein $R^{5g}$ and $R^{5h}$ is H or ($C_{1-6}$)alkyl; or $R^{5g}$ is H and $R^{5h}$ is ($C_{3-7}$) cycloalkyl, said alkyl and said cycloalkyl being optionally substituted with $COOR^{5i}$ wherein $R^{5i}$ is selected from the group consisting of:
    H and ($C_{1-6}$)alkyl;
    or $CONHNH_2$; or OH or ($C_{1-6}$)alkoxy; or ($C_{6-10}$) aryl; or 5- or 6-membered heterocycle having 1 to 4 heteroatom selected from O, N, and S, said heterocycle being optionally mono- or di-substituted with ($C_{1-6}$)alkyl;
    or $R^{5h}$ is $NR^{5j}R^{5k}$ wherein when $R^{5j}$ and $R^{5k}$ are both H; or $R^{5j}$ is H and $R^{5k}$ is $CH_2CF_3$;
    or $R^5h$ is 5- or 6-membered heterocycle having 1 to 4 heteroatoms selected from O, N, and S;
  (viii) $COR^{5l}$ wherein $R^{5l}$ is ($C_{1-6}$) alkyl or 5- or 6-membered heterocycle having 1 to 4 heteroatoms selected from O, N, and S, said heterocycle being optionally substituted with ($C_{1-6}$)alkyl;
  (ix) $SO_2R^{5m}$, wherein $R^5m$ is ($C_{1-6}$)alkyl or $NH_2$; and
  (x) $SO_3H$;
or $R^5$ is $COR^{5n}$ wherein $R^{5n}$ is ($C_{1-6}$) alkyl or 5- or 6-membered heterocycle having 1 to 4 heteroatom selected from O, N, and S, said heterocycle being optionally substituted with ($C_{1-6}$)alkyl;
$COOR^{5o}$ wherein $R^{5o}$ is ($C_{1-6}$) alkyl;
$CONR^{5p}R^{5q}$ wherein $R^{5p}$ and $R^{5q}$ is H, OH, ($C_{1-6}$)alkoxy, or ($C_{1-6}$)alkyl said alkyl being optionally substituted with ($C_{1-6}$)alkoxy, ($C_{6-10}$)aryl, 5- or 6-membered heterocycle having 1 to 4 heteroatom selected from O, N, and S, said heterocycle being optionally mono- or di-substituted with ($C_{1-6}$)alkyl; and
$COCH_2NR^{5r}R^{5s}$ wherein $R^{5r}$ and $R^{5s}$ is H or ($C_{1-6}$)alkyl, said alkyl being optionally substituted with ($C_{1-6}$) alkoxy, ($C_{6-10}$)aryl, or 5- or 6-membered heterocycle having 1 to 4 heteroatom selected from O, N, and S, said heterocycle being optionally mono- or di-substituted with ($C_{1-6}$)alkyl;
and each $R^8$ is independently H, ($C_{1-4}$) alkyl, ($C_{3-6}$) cycloalkyl, or ($C_{1-4}$) alkyl-($C_{3-6}$) cycloalkyl;
  b) E is $CR^{8a}R^{8b}$ wherein $R^{8a}$ and $R^{8b}$ is H, ($C_{1-4}$) alkyl, ($C_{3-6}$) cycloalkyl, or ($C_{1-4}$) alkyl-($C_{3-6}$) cycloalkyl, and J is $CH_2$; or J is $CR^{8a}R^{8b}$ wherein $R^{8a}$ and $R^{8b}$ are as defined above and E is $CH_2$, wherein the dotted line represents a single bond; or
  c) E is C(O) and J is $CR^{8a}R^{8b}$ wherein $R^{8a}$ and $R^{8b}$ are as described herein; or J is C(O) and E is $CR^{8a}R^{8b}$ wherein $R^{8a}$ and $R^{8b}$ are as described herein, wherein the dotted line represents a single bond; or
  d) both E and J are $CR^8$ wherein $R^8$ is as described herein, wherein the dotted line represents a double bond;

or a salt or a prodrug thereof.

Alternatively, according to a first aspect of the invention $R^5$ is selected from the group consisting of: H, ($C_{1-6}$)alkyl and ($C_{3-6}$) cycloalkyl, said alkyl being optionally substituted with a substituent selected from the group consisting of:
  (i) ($C_{3-6}$ cycloalkyl);
  (iii) $NR^aR^{5b}$, wherein $R^{5a}$ and $R^{5b}$ is H or ($C_{1-6}$)alkyl, said alkyl being optionally substituted with ($C_{1-6}$) alkoxy, ($C_{6-10}$)aryl, or 5- or 6-membered heterocycle having 1 to 4 heteroatom selected from O, N, and 3, said heterocycle being optionally mono- or di-substituted with ($C_{1-6}$)alkyl;
  (iv) $OR^{5c}$ wherein $R^{5c}$ is H, ($C_{1-6}$) alkyl;
  (vi) $COOR^{5f}$, wherein $R^{5f}$ is H or ($C_{1-6}$)alkyl;
  (vii) $CONR^{5g}R^{5h}$ wherein $R^{5g}$ and $R^{5h}$h is H or ($C_{1-6}$) alkyl; or $R^{5g}$ is H and $R^{5h}$ is ($C_{1-6}$)alkyl said alkyl being optionally substituted with ($C_{1-6}$)alkoxy, ($C_{6-10}$)aryl, or 5- or 6-membered heterocycle having 1 to 4 heteroatom selected from O, N, and S, said heterocycle being optionally mono- or di-substituted with ($C_{1-6}$)alkyl;
or $R^5$ is $COR^{5n}$ wherein $R^{5n}$ is ($C_{1-6}$) alkyl;
$COOR^{5o}$ wherein $R^{5o}$ is ($C_{1-6}$) alkyl;
$CONR^{5p}PR^{5q}$ wherein $R^{5p}$ and $R^{5q}$ is H, OH, ($C_{1-6}$) alkoxy, ($C_{1-6}$)alkyl, said alkyl being optionally substituted with ($C_{1-6}$)alkoxy, ($C_{6-10}$)aryl, or 5- or 6-membered heterocycle having 1 to 4 heteroatom selected from O, N, and S, said heterocycle being optionally mono- or di-substituted with ($C_{1-6}$)alkyl; and
$COCH_2NR^{5r}R^{5s}$ wherein $R^{5r}$ and $R^{5s}$ is H or ($C_{1-6}$)alkyl said alkyl being optionally substituted with ($C_{1-6}$) alkoxy, ($C_{6-10}$)aryl, or 5- or 6-membered heterocycle having 1 to 4 heteroatom selected from O, N, and S, said heterocycle being optionally mono- or di-substituted with ($C_{1-6}$)alkyl.

According to a second aspect of the invention, there is provided a method for the treatment or prevention of HIV infection, comprising administering to a patient an HIV inhibiting amount of a compound of formula I as described herein, or a pharmaceutically acceptable salt thereof.

According to a third aspect of the invention, there is provided a pharmaceutical composition for the treatment or prevention of HIV infection, comprising a compound of formula I, as described herein, or a pharmaceutically acceptable salt thereof, and a pharmaceutically acceptable carrier.

According to a fourth aspect of the invention, there is provided a method for treating or preventing HIV infection comprising administering a compound of formula I, as described herein, in combination with an antiretroviral drug.

According to a fifth aspect of the invention, there is provided a method for preventing perinatal transmission of HIV-1 from mother to baby, comprising administering a compound of formula I, as described herein, to the mother before giving birth.

According to a sixth aspect of the invention, there is provided a process for producing a compound of formula I:

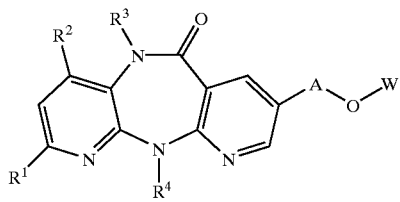

wherein A, $R^1$, $R^2$, $R^3$, $R^4$ and W are as described herein, comprising:

a) removing, in a mixture of an aqueous base or an aqueous acid in a co-solvent, the protecting group (PG) from:

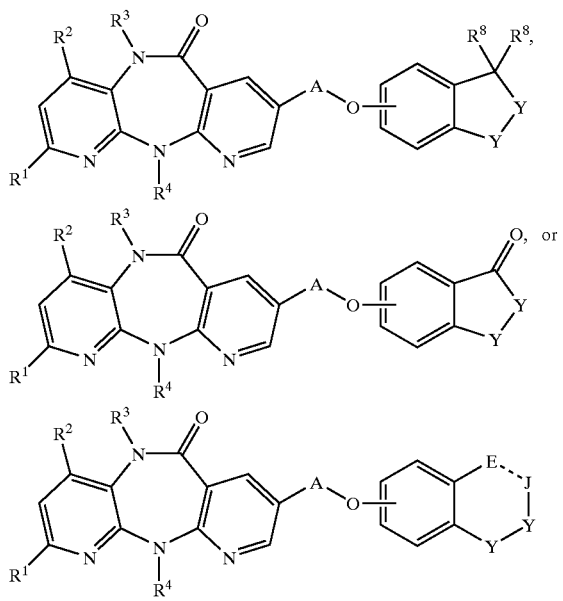

wherein one of Y is $SO_2$ and the other Y is N-PG, wherein PG is an amino protecting group removable under mildly acidic, alkaline or reductive conditions, to produce compounds of formula I, wherein E, J and $R^8$ are as described herein.

According to an seventh of the invention, there is provided a process for producing a compound of formula I:

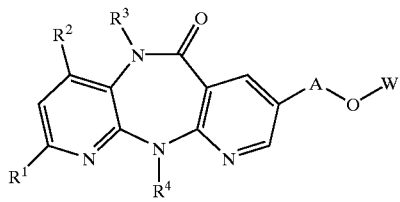

wherein A, $R^1$, $R^2$, $R^3$, $R^4$ and W are as described herein, comprising:

a) coupling a compound of formula 2

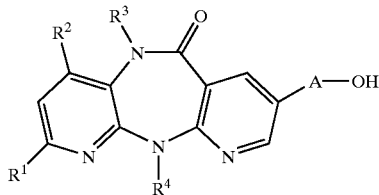

wherein A, $R^1$, $R^2$, $R^3$, and $R^4$ are as described herein, with a sultam or a saccharin selected from:

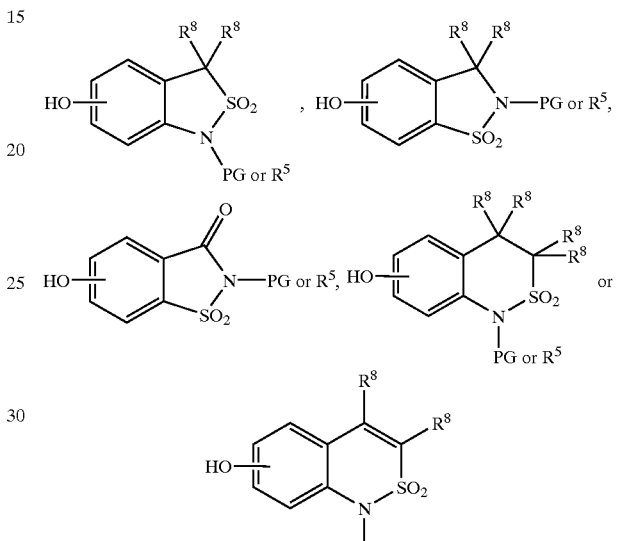

wherein PG is a nitrogen protecting group removable under mildly acidic, alkaline or reductive conditions; and $R^5$ and $R^8$ are as described herein, to produce compounds of formula 1.

DETAILED DESCRIPTION OF THE INVENTION

The following definitions apply unless otherwise noted:

As used herein, the terms "$(C_{1-3})$ alkyl", "$(C_{1-4})$ alkyl" or "$(C_{1-6})$ alkyl", either alone or in combination with another radical, are intended to mean acyclic alkyl radicals containing up to three, four and six carbon atoms respectively. Examples of such radicals include methyl, ethyl, propyl, butyl, hexyl, 1-methylethyl, 1-methylpropyl, 2-methylpropyl, 1,1-dimethylethyl.

As used herein. the term "$(C_{3-7})$ cycloalkyl", either alone or in combination with another radical, means a cycloalkyl radical containing from three to seven carbon atoms and includes cyclopropyl, cyclobutyl, cyclopentyl, cyclohexyl and cycloheptyl.

As used herein, the term "$(C_{6-10})$ aryl", either alone or in combination with another radical means aromatic radical containing from six to ten carbon atoms, for example phenyl.

As used herein, the term "$(C_{1-6})$ alkoxy", either alone or in combination with another radical, refers to the radical —O($C_{1-6}$ alkyl) wherein alkyl is as defined above containing up to six carbon atoms. Examples include methoxy, ethoxy, propoxy, 1-methylethoxy, butoxy and 1,1-dimethylethoxy.

As used herein, the term "heterocycle" or "Het", either alone or in combination with another radical, means a monovalent radical derived by removal of a hydrogen from a five-, six-, or seven-membered saturated or unsaturated (including aromatic) heterocycle containing from one to four heteroatoms selected from nitrogen, oxygen and sulfur. Furthermore, "Het" as used herein, means a heterocycle as defined above fused to one or more other cycle, be it a heterocycle or any other cycle. The heterocycles may be substituted. Examples of such substituents include, but are not limited to, halogen, amines, hydrazines and N-oxido. Examples of suitable heterocycles include: pyrrolidine, tetrahydrofuran, thiazolidine, pyrrole, thiophene, diazepine, 1H-imidazole, isoxazole, thiazole, tetrazole, piperidine, 1,4-dioxane, 4-morpholine, pyridine, pyrimidine, thiazolo[4,5-b]-pyridine, quinoline, or indole, or the following heterocycles:

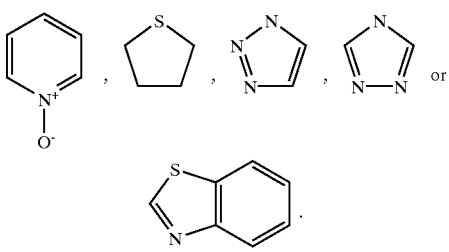

As used herein, the term "halo" means a halogen atom and includes fluorine, chlorine, bromine and iodine.

As used herein, the term "inhibitor of HIV replication" means that the ability of HIV-1 reverse transcriptase to replicate a DNA copy from an RNA template is substantially reduced or essentially eliminated.

As used herein, the term "single or double mutant strains" means that either one or two amino acid residues that are present in WT HIV-1 strain have been replaced by residues not found in the WT strain. For example, the single mutant Y181 C is prepared by site-directed mutagenesis in which the tyrosine at residue 181 has been replaced by a cysteine residue. Similarly, for the double mutant K103N/Y181C, an asparagine residue has replaced the lysine at residue 103 and a cysteine residue has replaced the tyrosine at residue 181.

As used herein, the term "pharmaceutically acceptable salt" includes those derived from pharmaceutically acceptable bases and is non-toxic. Examples of suitable bases include choline, ethanolamine and ethylenediamine. Na+, K+, and Ca++ salts are also contemplated to be within the scope of the invention (also see Pharmaceutical salts, Birge, S. M. et al., J. Pharm. Sci., (1977), 66, 1–19, incorporated herein by reference).

As used herein, the term "nitrogen protecting group" means a group capable of protecting a nitrogen atom against undesirable reactions during synthetic procedures (see "Protective Groups in Organic Synthesis", Theodora W. Greene and Peter G. M. Wuts, third edition, 1999).

As used herein, the term "prodrug" refers to pharmacologically acceptable derivatives, such that the resulting biotransformation product of the derivative is the active drug, as defined in compounds of formula I. Examples of such derivatives include, but are not limited to, esters and amides. (see Goodman and Gilman in The Pharmacological Basis of Therapeutics, 9$^{th}$ ed., McGraw-Hill, Int. Ed. 1995, "Biotransformation of Drugs, p 11–16, incorporated herein by reference).

Preferred Embodiments

According to the first embodiment of the invention, preferably compounds have the following formula:

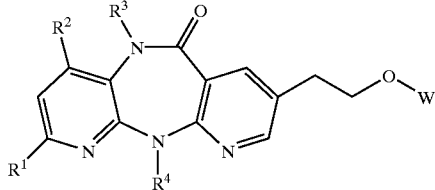

Preferably, $R^1$ is H, $(C_{1-6})$alkyl, halo or $CF_3$. More preferably, $R^1$ is H, $(C_{1-6})$alkyl or F. Even more preferably, $R^1$ is H, methyl or F. Most preferably, $R^1$ is H or F.

Preferably, $R^2$ is H or Me. More preferably, $R^2$ is H

Preferably, $R^3$ is H or Me. More preferably, $R^3$ is $CH_3$.

Preferably, $R^4$ is selected from H, $(C_{1-4})$ alkyl and $(C_{3-4})$ cycloalkyl. More preferably, $R^4$ is $(C_{1-4})$ alkyl and $(C_{3-4})$ cycloalkyl. Even more preferably, $R^4$ is Et or cyclopropyl. Most preferably, $R^4$ is Et.

Preferably, W is

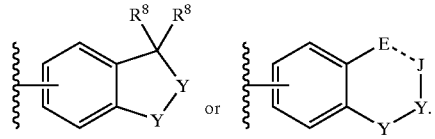

Preferably, one of Y is $SO_2$ and the other Y is $NR^5$, provided that both are not the same.

Preferably, E is $CR^{8a}R^{8b}$ wherein $R^{8a}$ and $R^{8b}$ is H, $(C_{1-4})$ alkyl, $(C_{3-6})$ cycloalkyl, or $(C_{1-4})$ alkyl-$(C_{3-6})$ cycloalkyl, and J is $CH_2$; or J is $CR^{8a}R^{8b}$ wherein $R^{8a}$ and $R^{8b}$ are as defined above and E is $CH_2$, wherein the dotted line represents a single bond.

Preferably, both E and J are $CR^8$ wherein $R^8$ is as described herein, wherein the dotted line represents a double bond.

Preferably $R^5$ is selected from the group consisting of: H, $(C_{1-6})$alkyl, said alkyl being optionally substituted with a substituent selected from the group consisting of:
(i) ($C_{3-6}$ cycloalkyl);
(ii) 5- or 6-membered heterocycle having 1 to 4 heteroatom selected from O, N, and S, said heterocycle being optionally substituted with $(C_{1-6})$alkyl;
(iii) $NR^{5a}R^{5b}$, wherein $R^{5a}$ and $R^{5b}$ is H or $(C_{1-6})$alkyl;
(iv) $OR^{5c}$ wherein $R^{5c}$ is H, $(C_{1-6})$ alkyl or 5- or 6-membered heterocycle having 1 to 4 heteroatom selected from O, N, and S;
(v) $OCONR^{5d}R^{5e}$, wherein $R^{5d}$ and $R^{5e}$ are both H; or $R^{5d}$ is H and $R^{5e}$ is $(C_{1-6})$alkyl;
(vi) $COOR^{5f}$, wherein $R^{5f}$ is H or $(C_{1-6})$alkyl;
(vii) $CONR^{5g}R^{5h}$ wherein $R^{5g}$ and $R^{5h}$ is H or $(C_{1-6})$ alkyl; or $R^{5g}$ is H and $R^{5h}$ is $(C_{3-7})$cycloalkyl, said alkyl and said cycloalkyl being optionally substituted with $COOR^{5i}$ wherein $R^{5i}$ is selected from the group consisting of:
H and $(C_{1-6})$alkyl; or $CONHNH_2$;
or $R^{5h}$ is $NH_2$ or $NHCH_2CF_3$;
or $R^{5h}$ is 5- or 6-membered heterocycle having 1 to 4 heteroatoms selected from O, N, and S;
(viii) $COR^{5l}$ wherein $R^{5l}$ is $(C_{1-6})$ alkyl or 5- or 6-membered heterocycle having 1 to 4 heteroatoms selected from O, N, and S, said heterocycle being optionally substituted with $(C_{1-6})$alkyl;
(ix) $SO_2R^{5m}$, wherein $R^{5m}$ is $(C_{1-6})$alkyl or $NH_2$; and (x) SO$_3$H;

or R$^5$ is COR$^{5n}$ wherein R$^{5n}$ is (C$_{1-6}$) alkyl or 5- or 6-membered heterocycle having 1 to 4 heteroatoms selected from O, N, and S, said heterocycle being optionally substituted with (C$_{1-6}$)alkyl;

COOR$^{5o}$ wherein R$^{5o}$ is (C$_{1-6}$) alkyl; and

CONR$^{5p}$R$^{5q}$ wherein R$^{5p}$ and R$^{5q}$ is H, (C$_{1-6}$)alkyl, OH or (C$_{1-6}$)alkoxy.

More preferably, R$^5$ is H or (C$_{1-6}$)alkyl said alkyl being optionally substituted with a substituent selected from the group consisting of:

(i) (C$_{3-6}$ cycloalkyl);
(ii) 5- or 6-membered heterocycle having 1 to 4 heteroatoms selected from O, N, and S, said heterocycle being optionally substituted with (C$_{1-6}$)alkyl;
(iii) NR$^{5a}$R$^{5b}$, wherein R$^{5a}$ and R$^{5b}$ is H or (C$_{1-6}$)alkyl;
(iv) OH;
(vi) COOR$^{5f}$, wherein R$^{5f}$ is H or (C$_{1-6}$)alkyl;
(vii) CONR$^{5g}$R$^{5h}$ wherein R$^{5g}$ and R$^{5h}$ are both H; or R$^{5g}$ is H and R$^5$h is NH$_2$; and
(viii) COR$^{5l}$ wherein R$^{5l}$ is (C$_{1-6}$) alkyl or 5- or 6-membered heterocycle having 1 to 4 heteroatoms selected from O, N, and S, said heterocycle being optionally substituted with (C$_{1-6}$)alkyl;

or R$^5$ is COR$^{5n}$ wherein R$^{5n}$ is (C$_{1-6}$) alkyl or 5- or 6-membered heterocycle having 1 to 4 heteroatoms selected from O, N, and S, said heterocycle being optionally substituted with (C$_{1-6}$)alkyl;

COOR$^{5o}$ wherein R$^{5o}$ is (C$_{1-6}$) alkyl; and

CONR$^{5p}$ R$^{5q}$ wherein R$^{5p}$ and R$^{5q}$ is (C$_{1-6}$)alkyl or (C$_{1-6}$)alkoxy.

Most preferably, R$^5$ is selected from the group consisting of: H, (C$_{1-6}$)alkyl, wherein said alkyl is optionally substituted with COOH.

Preferably, each R$^8$ is each independently H, (C$_{1-4}$) alkyl. More preferably, each of R$^8$ is H or CH$_3$ Most preferably, each of R$^8$ is H.

Preferably W is:

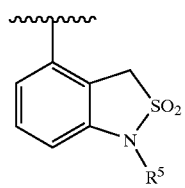

I(b)

wherein R$^5$ is preferably selected from the group consisting of: H, (C$_{1-6}$)alkyl, said alkyl being optionally substituted with a substituent selected from the group consisting of:

(i) (C$_{3-6}$)cycloalkyl;
(ii) 5- or 6-membered heterocycle having 1 to 4 heteroatoms selected from O, N, and S, said heterocycle being optionally substituted with (C$_{1-6}$)alkyl;
(iv) OH; and
(vi) COOR$^{5f}$, wherein R$^{5f}$ is H or (C$_{1-6}$)alkyl;
and COOR$^{5o}$ wherein R$^{5o}$ is (C$_{1-6}$) alkyl.

More preferably, R$^5$ is selected from the group consisting of: H, CH$_3$, CH$_3$CH$_2$,

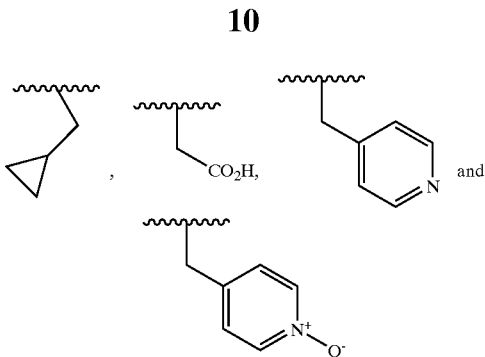

Most preferably, R$^5$ is selected from the group consisting of: H, CH$_3$, CH$_3$CH$_2$,

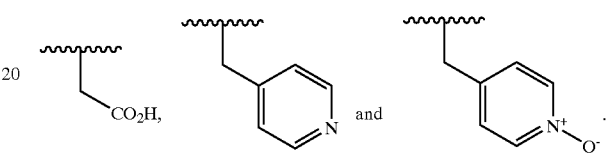

Preferably, R$^{5f}$ is H.

Preferably, R$^{5o}$ is (C$_{1-6}$)alkyl. More preferably, R$^{5o}$ is ethyl.

Preferably W is:

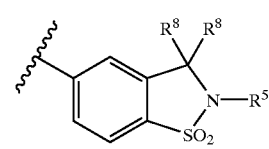

I(c)

wherein R$^5$ is H, (C$_{1-6}$)alkyl, and preferably, each of R$^8$ is H or CH$_3$. Most preferably R$^5$ is H or CH$_3$.

Preferably W is

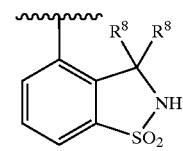

I(d)

wherein preferably, each of R$^8$ is H or CH$_3$

Preferably, W is:

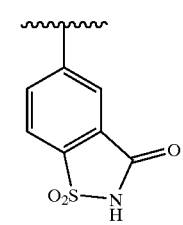

I(f)

Alternatively preferably, W is:

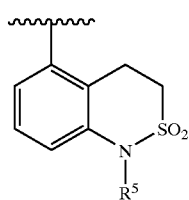

I(g)

wherein preferably $R^5$ is selected from the group consisting of: H, $(C_{1-6})$alkyl, said alkyl being optionally substituted with a substituent selected from the group consisting of:
  (ii) 5- or 6-membered heterocycle having 1 to 4 heteroatoms selected from O, N, and S, said heterocycle being optionally substituted with $(C_{1-6})$alkyl;
  (iii) $NR^{5a}R^{5b}$, wherein $R^{5a}$ and $R^{5b}$ is H or $(C_{1-6})$alkyl;
  (iv) OH or $(C_{1-6})$alkoxy;
  (vi) $COOR^{5f}$, wherein $R^{5f}$ is H or $(C_{1-6})$alkyl; or
  (vii) $CONH_2$; and
  (viii) $COR^{5l}$ wherein $R^{5l}$ is $(C_{1-6})$ alkyl or 5- or 6-membered heterocycle having 1 to 4 heteroatoms selected from O, N, and S, said heterocycle being optionally substituted with $(C_{1-6})$alkyl;
or $R^5$ is $COR^{5n}$ wherein $R^{5n}$ is $(C_{1-6})$ alkyl or 5- or 6-membered heterocycle having 1 to 4 heteroatoms selected from O, N, and S, said heterocycle being optionally substituted with $(C_{1-6})$alkyl; and
$CONR^{5p}R^{5q}$ wherein $R^{5p}$ and $R^{5q}$ is H, $(C_{1-6})$alkyl, OH or $(C_{1-6})$alkoxy.

Preferably $R^5$ is selected from the group consisting of:

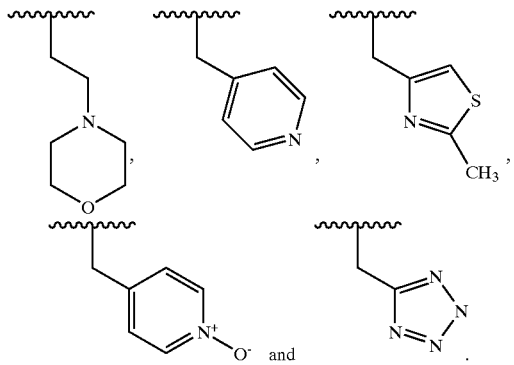

Alternatively preferably, $R^5$ is selected from the group consisting of:

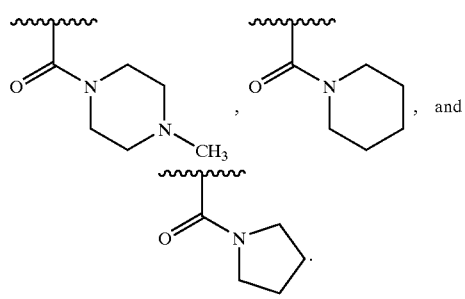

Preferably both $R^{5a}$ and $R^{5b}$ are both $(C_{1-6})$alkyl. More preferably, both $R^{5a}$ and $R^{5b}$ are ethyl.
Preferably, $R^5$ is OH.

Preferably $R^{5f}$ is H or methyl.
Preferably, $R^{5l}$ is

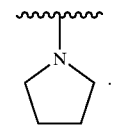

Preferably $R^{5p}$ and $R^{5q}$ are both $(C_{1-6})$alkyl. More preferably, both $R^{5p}$ and $R^{5q}$ are both ethyl.
Alternatively preferably, when $R^{5p}$ is $(C_{1-6})$alkyl, then $R^{5q}$ is OH or $(C_{1-6})$alkoxy. More preferably, $R^{5p}$ is methyl and $R^{5q}$ is $(C_{1-6})$alkoxy.
Preferably, $R^{5q}$ is $OCH_3$.
Preferably W is:

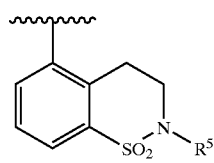

I(h)

wherein preferably $R^5$ is H, $(C_{1-6})$alkyl wherein said alkyl is substituted with a substituent selected from the group consisting of:
  (vi) $COOR^{5f}$, wherein $R^{5f}$ is H or $(C_{1-6})$alkyl; and
  (vii) $CONHNH_2$.
Preferably, $R^5$ is $(CH_2)_3COOH$ and $(CH_2)_3CONHNH_2$.
Preferably W is

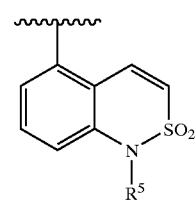

I(i)

wherein preferably $R^5$ is selected from the group consisting of: H, $(C_{1-6})$alkyl and $(CH_2)_3COOH$.
More preferably, $R^5$ is H or $CH_3$.
Preferably, compounds of the invention are of the formula:

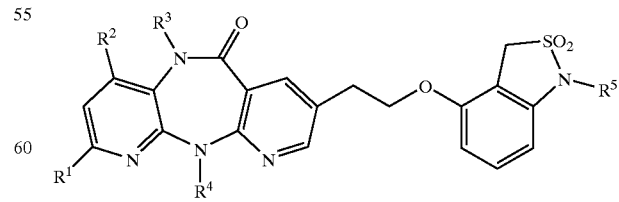

wherein $R^1$, $R^2$, $R^3$, $R^4$ and $R^5$ are as described above.
Alternatively preferably, compounds of the invention are of the formula:

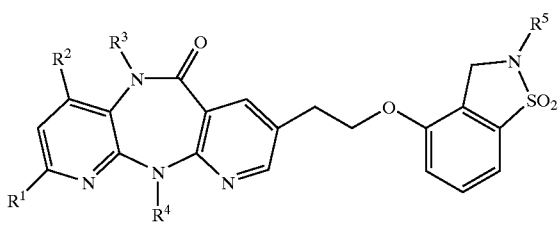

wherein $R^1$, $R^2$, $R^3$, $R^4$ and $R^5$ are as described above.

Alternatively preferably, compounds of the invention are of the formula:

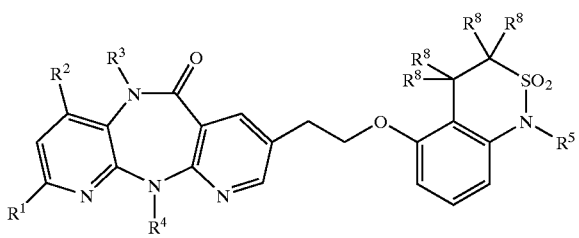

wherein $R^1$, $R^2$, $R^3$, $R^4$, $R^5$ and $R^8$ are as described above.

Alternatively preferably, compounds of the invention are of the formula:

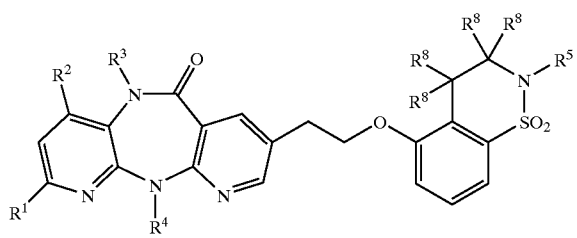

wherein $R^1$, $R^2$, $R^3$, $R^4$, $R^5$ and $R^8$ are as described above.

Alternatively preferably, compounds of the invention are of the formula:

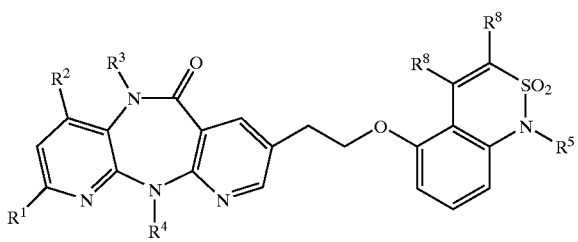

wherein $R^1$, $R^2$, $R^3$, $R^4$, $R^5$ and $R^8$ are as described above.

Specific Embodiments

Included within the scope of this invention are all compounds of Formula I as presented in Tables 1 to 8.

The compounds of formula I are effective inhibitors of wild type HIV as well as inhibiting the double mutation enzyme K103N/Y181C. The compounds of the invention may also inhibit the single mutation enzymes V106A, Y188L, k103N, Y181C, P236L and G190A. The compounds may also inhibit other double mutation enzymes including K103N/P225H, K103N/V108 I and K103N/L100I.

The compounds of formula I possess inhibitory activity against HIV-1 replication. When administered in suitable dosage forms, they are useful in the treatment of AIDS, ARC and related disorders associated with HIV-1 infection. Another aspect of the invention, therefore, is a method for treating HIV-1 infection which comprises administering to a human being, infected by HIV-1, a therapeutically effective amount of a novel compound of formula I, as described above. Whether it is termed treatment or prophylaxis, the compounds may also be used to prevent perinatal transmission of HIV-1 from mother to baby, by administration to the mother before giving birth.

The compounds of formula I may be administered in single or divided doses by the oral, parenteral or topical routes. A suitable oral dosage for a compound of formula 1would be in the range of about 0.5 mg to 1 g per day. A preferred oral dosage for a compound of formula I would be in the range of about 100 mg to 800 mg per day for a patient weighing 70 kg. In parenteral formulations, a suitable dosage unit may contain from 0.1 to 250 mg of said compounds, preferably 1 mg to 200 mg, whereas for topical administration, formulations containing 0.01 to 1% active ingredient are preferred. It should be understood, however, that the dosage administration from patient to patient would vary. The dosage for any particular patient will depend upon the clinician's judgement, who will use as criteria for fixing a proper dosage the size and condition of the patient as well as the patient's response to the drug. When the compounds of the present invention are to be administered by the oral route, they may be administered as medicaments in the form of pharmaceutical preparations that contain them in association with a compatible pharmaceutical carrier material. Such carrier material can be an inert organic or inorganic carrier material suitable for oral administration. Examples of such carrier materials are water, gelatin, talc, starch, magnesium stearate, gum arabic, vegetable oils, polyalkyleneglycols, petroleum jelly and the like.

The compounds of formula I can be used in combination with an antiretroviral drug known to one skilled in the art, as a combined preparation useful for simultaneous, separate or sequential administration for treating or preventing HIV infection in an individual. Examples of antiretroviral drugs that may be used in combination therapy with compounds of formula I, include but are not limited to, NRTIs (such as AZT), NNRTI's (such as Nevirapine), compounds of the TIBO (tetrahydroimidazo[4,5,1-jk][1,4]-benzodiazepine-2 (1H)-one and thione)-type, compounds of the α-APA (α-anilino phenyl acetamide)-type, TAT inhibitors, protease inhibitors (such as Ritanovir), and immunomodulating agents (such as Levamisole). Moreover, a compound of formula I can be used with another compound of formula I.

The pharmaceutical preparations can be prepared in a conventional manner and finished dosage forms can be solid dosage forms, for example, tablets, dragees, capsules, and the like, or liquid dosage forms, for example solutions, suspensions, emulsions and the like. The pharmaceutical preparations may be subjected to conventional pharmaceutical operations such as sterilization. Further, the pharmaceutical preparations may contain conventional adjuvants such as preservatives, stabilizers, emulsifiers, flavor-improvers, wetting agents, buffers, salts for varying the osmotic pressure and the like. Solid carrier material which can be used include, for example, starch, lactose, mannitol, methyl cellulose, microcrystalline cellulose, talc, silica, dibasic calcium phosphate, and high molecular weight polymers (such as polyethylene glycol).

For parenteral use, a compound of formula I can be administered in an aqueous or non-aqueous solution, suspension or emulsion in a pharmaceutically acceptable oil or a mixture of liquids, which may contain bacteriostatic agents, antioxidants, preservatives, buffers or other solutes to render the solution isotonic with the blood, thickening agents, suspending agents or other pharmaceutically acceptable additives. Additives of this type include, for example, tartrate, citrate and acetate buffers, ethanol, propylene glycol, polyethylene glycol, complex formers (such as EDTA), antioxidants (such as sodium bisulfite, sodium metabisulfite, and ascorbic acid), high molecular weight polymers (such as liquid polyethylene oxides) for viscosity regulation and polyethylene derivatives of sorbitol anhydrides. Preservatives may also be added if necessary, such as benzoic acid, methyl or propyl paraben, benzalkonium chloride and other quaternary ammonium compounds.

The compounds of this invention may also be administered as solutions for nasal application and may contain in addition to the compounds of this invention suitable buffers, tonicity adjusters, microbial preservatives, antioxidants and viscosity-increasing agents in an aqueous vehicle. Examples of agents used to increase viscosity are polyvinyl alcohol, cellulose derivatives, polyvinylpyrrolidone, polysorbates or glycerin. Microbial preservatives added may include benzalkonium chloride, thimerosal, chloro-butanol or phenylethyl alcohol.

Additionally, the compounds provided by the invention may be administerable by suppository.

Methodology and Synthesis

The compounds of the present invention were synthesised according to a general process as illustrated in Scheme I (wherein PG is a nitrogen-protecting group, $R^1$, $R^2$, $R^3$, and $R^4$ are as previously defined).

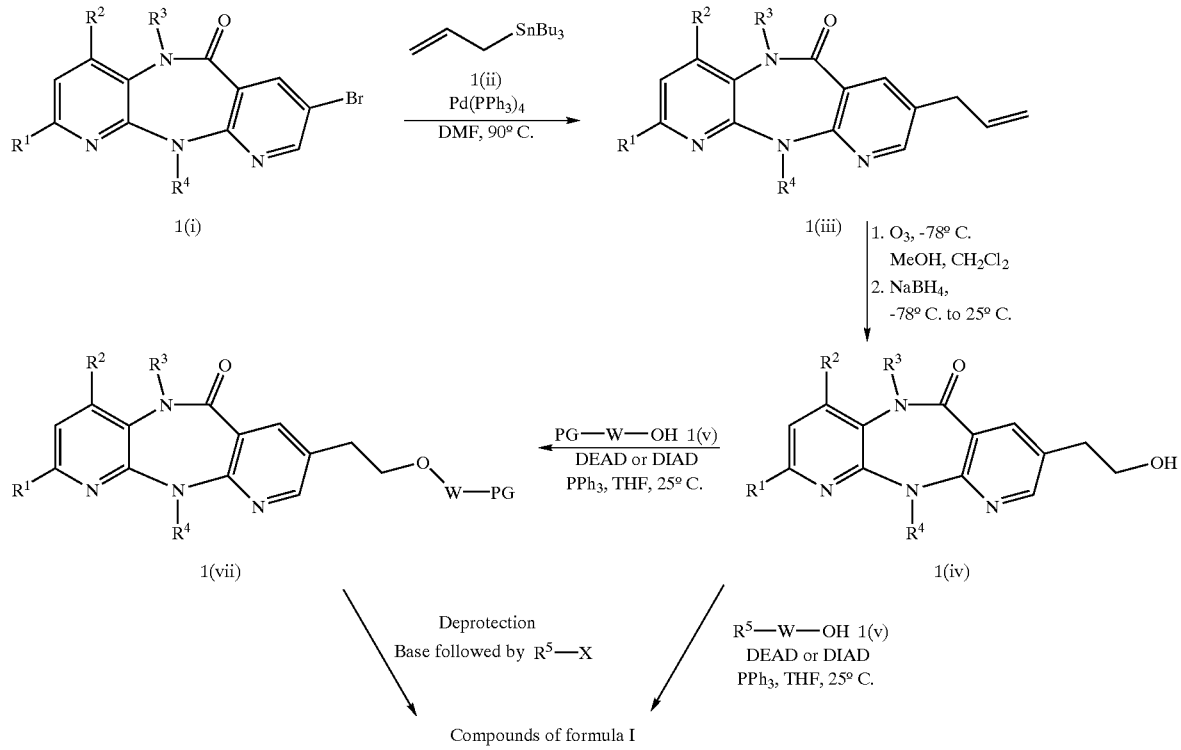

Briefly, condensation of 8-bromo-benzodiazepine 1(i), synthesized as described below, via a palladium-mediated cross coupling with allyl tin reagent 1(ii) in an aprotic solvent (e.g. DMF) and in the presence of a catalyst, forms C-8 substituents 1(iii). Oxidation of the double bond (e.g. by ozonolysis to produce an ozonide), followed by a reduction, produces the C-8 hydroxyethyl substituent 1(iv). Condensing a suitably protected sultam 1(v) with 1(iv) produces a protected intermediate (vii). The protecting group (PG) from 1(vii) may then removed under mild acidic or mild alkaline conditions giving compounds of formula I. Alternatively, after the protecting group has been removed, $R^5$ can be introduced using a base followed by reaction with $R^5$—X in which X is a halogen or some other suitable leaving group. Another alternative route may be used in which an $R^5$-contain sultam 1 (vi) is condensed with 1(iv) to give compounds of formula 1.

Other methods for introducing the C-8 substituents are known to one of ordinary skill in the art. Examples of such methods include vinylation at the C-8 position followed by hydroboration to give the C-8 hydroxyethylbenzodiazepine. A further example would be an $S_NAR$ reaction with an appropriately substituted aromatic sultam.

Scheme 2: Alternative introduction of the sultam

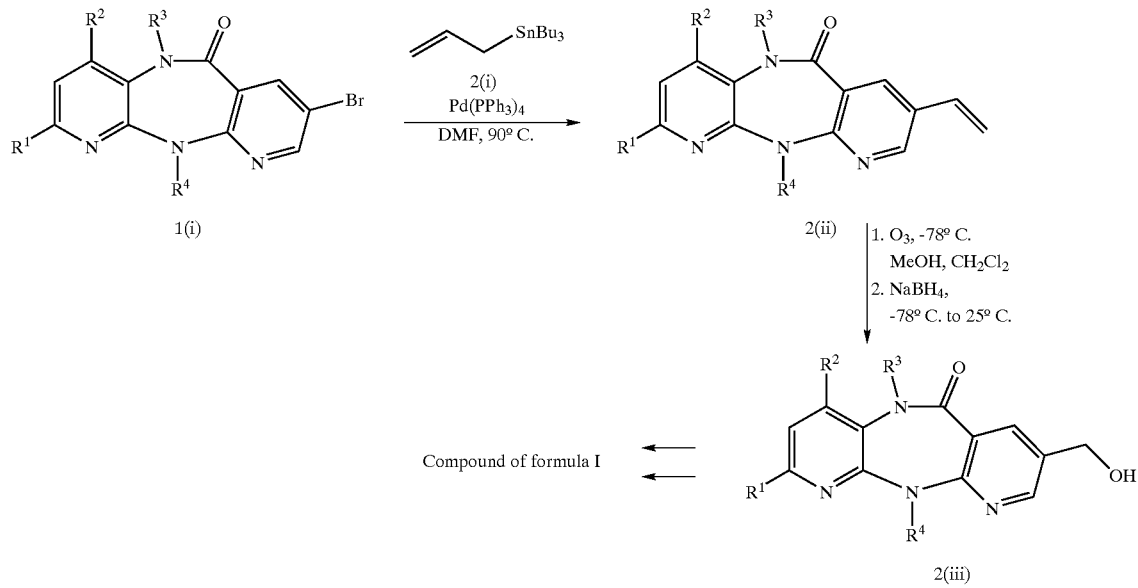

The chemistry illustrated in Scheme 2 is essentially the same as that described for Scheme 1 above. The difference being the use of the vinyl tin reagent 2(i) to give the vinylated intermediate 2(ii).

Sultam Synthesis

Synthesis of 5- and 6-membered sultam rings of the present invention use art-recognized chemistry. Schemes 3 to 5 below illustrate the methods used to prepare sultam rings of the present invention.

Scheme 3: Preparation of five-membered sultams

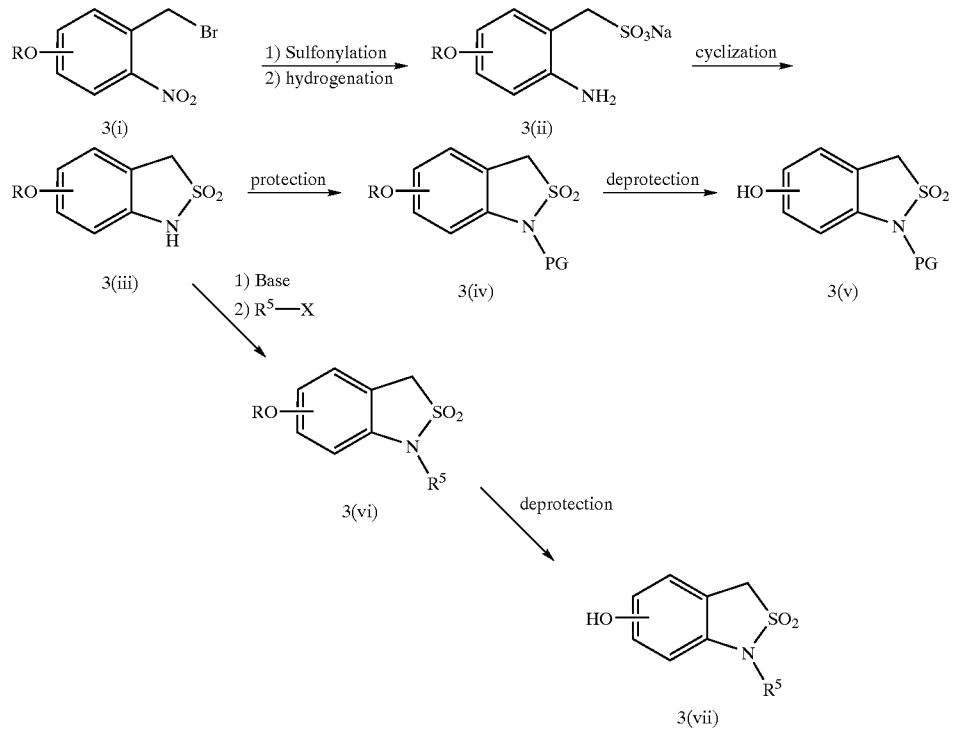

Briefly, commercially available bromo compound 3(i) is sulfonylated and the nitro group is reduced (e.g. by hydrogenation) to give the aniline intermediate 3(ii). Cyclization under alkaline conditions furnishes the sultam 3(iii). Protection of the sulfonamido group in sultam 3(iii)

gives sultam 3(iv), thereafter unmasking the OH group produces sultams 3(v) that are used to synthesize compounds of formula I. Alternatively, $R^5$ can be introduced into 3(iii) by a base-mediated addition reaction to furnish 3(vi) which, after unmasking the OH group, may used to produce compounds of the invention.

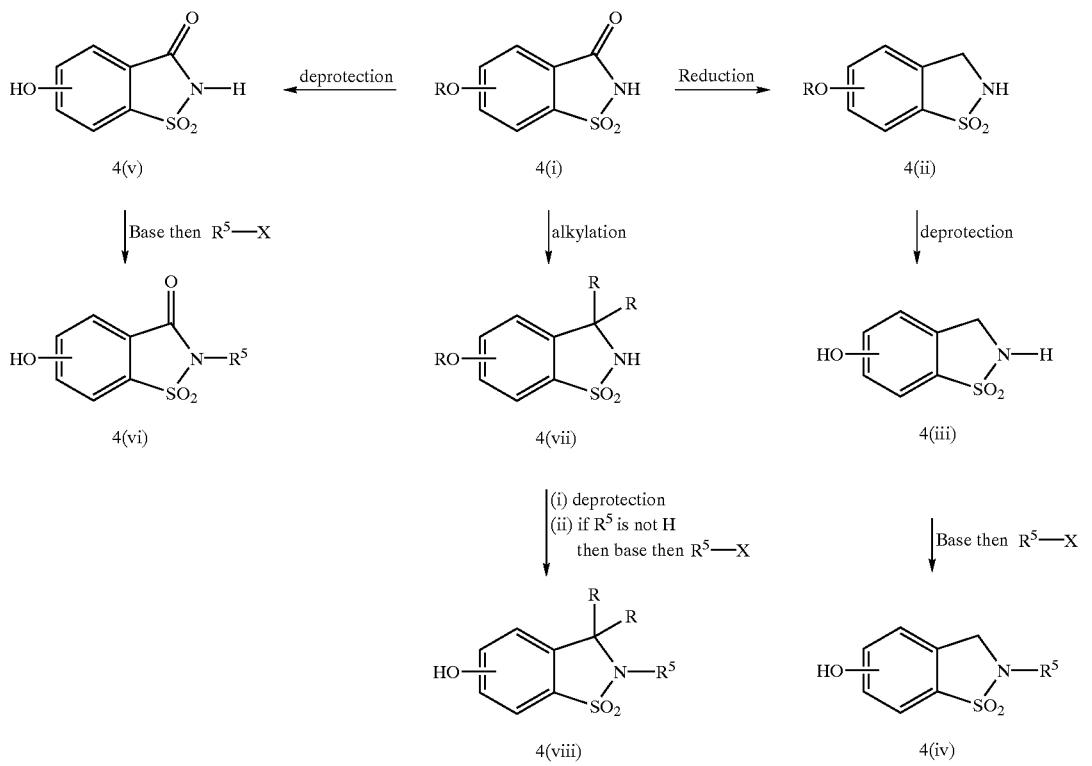

Generally, saccharin 4(i) (Lombardino, J. G., *J. Org. Chem.*, 1971, 1843), is reduced to give sultam 4(ii). Unmasking the OH group as previously described in Scheme 3, gives 4(iii), thereafter the $R^5$ group is added to give 4(iv). Alternatively, saccharin 4(i) may be alkylated to give sultam 4(vii) followed by unmasking the OH group to give 4(viii) or for compounds in which RI is not H, then $R^5$ can be introduced to give 4(viii). Moreover, the OH group in 4(i) may be unmasked followed by introduction of $R^5$ to give 4(vi). Sultams 4(iv), 4(vi), and 4(viii) can then be used to synthesize compounds of formula I.

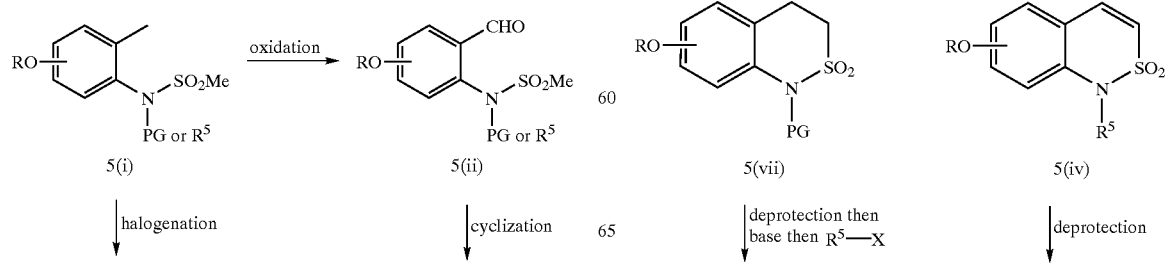

-continued

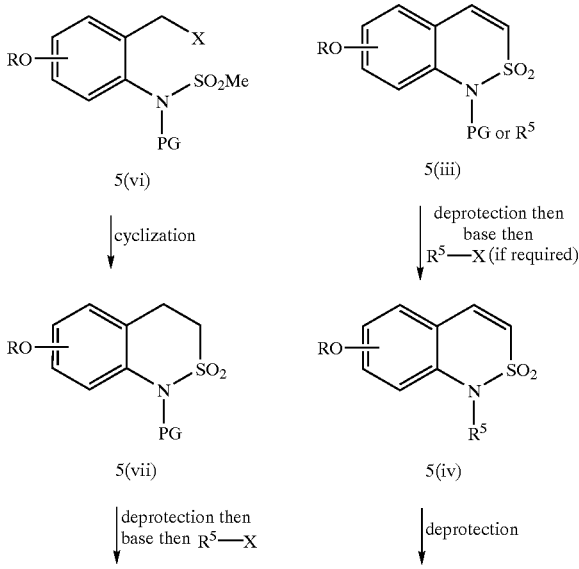

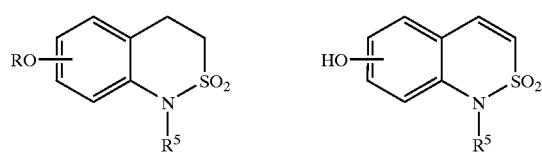
The above synthetic scheme is an adaptation of that disclosed by Blondet, D.; Pascal, J. -C. *Tetrahedron Lett.* 1994, 35, 2911.
Scheme 6: Preparation of intermediates in which $R^2$ is Me
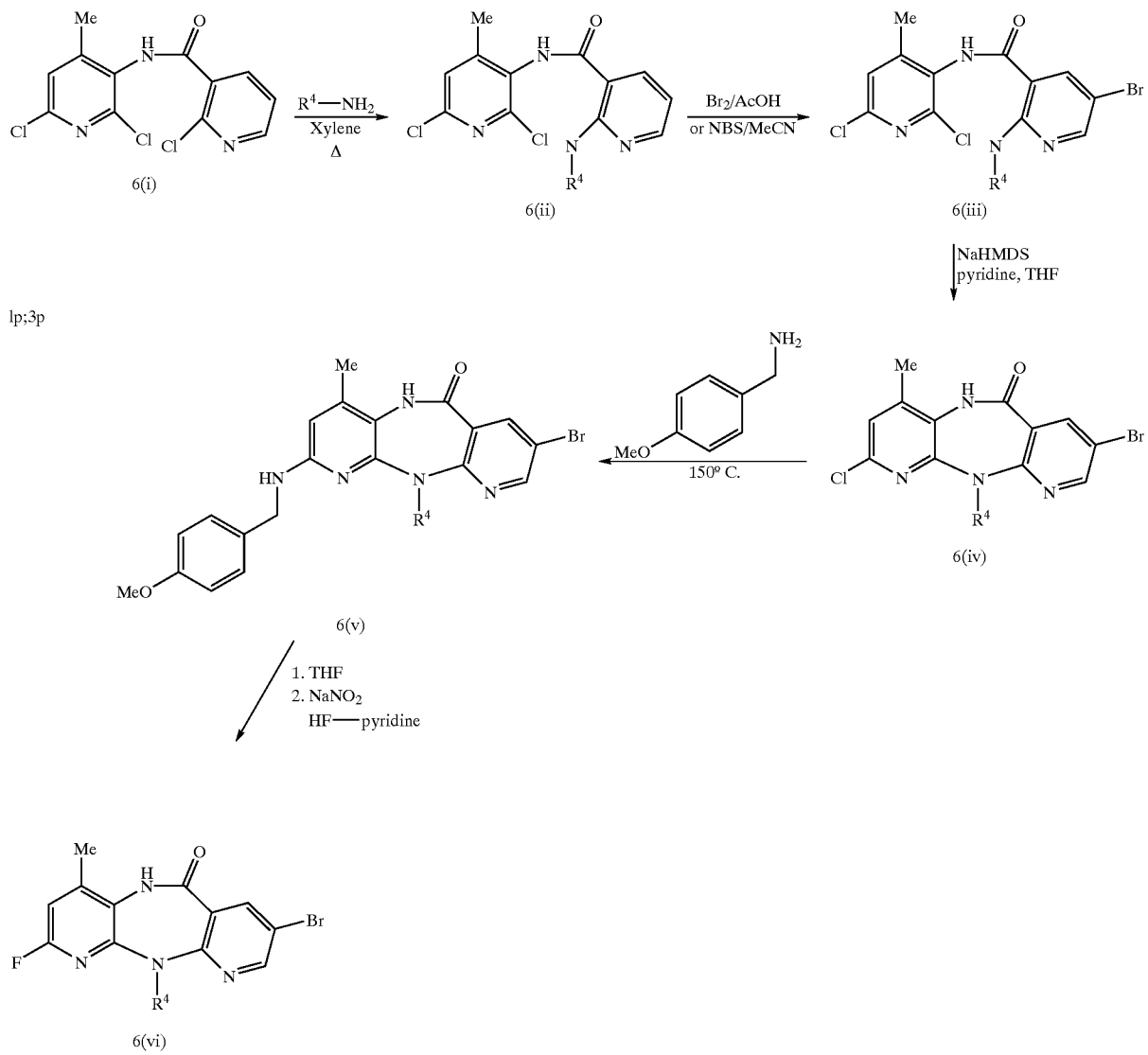

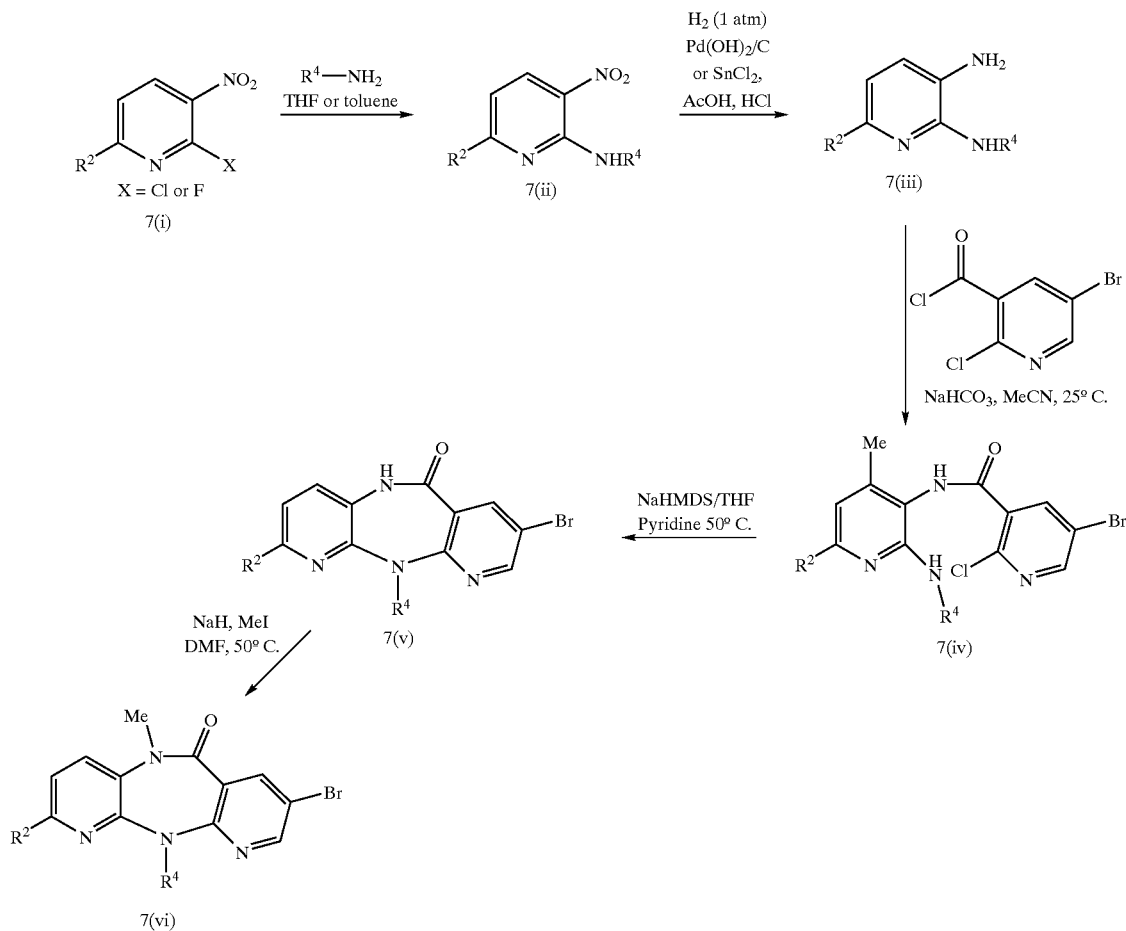
The sequence of scheme 7 is analogous to one described by V. M. Kiunder et al.; *J. Med. Chem.* 1998, 41, 2960–71, and C. L. Cywin et al.; *J. Med. Chem.* 1998, 41, 2972–84.
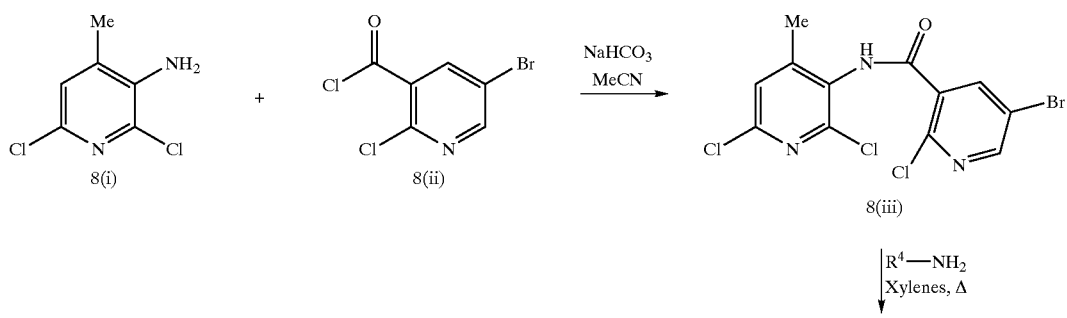

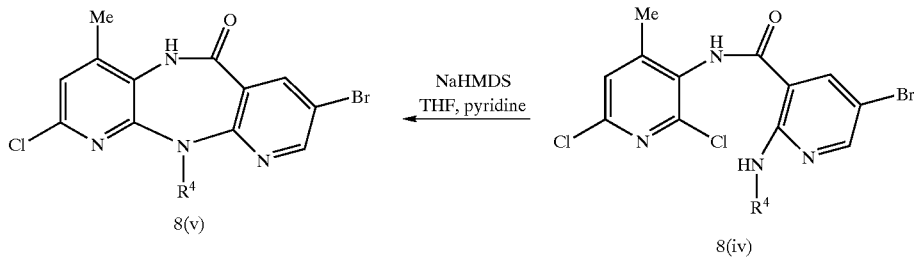

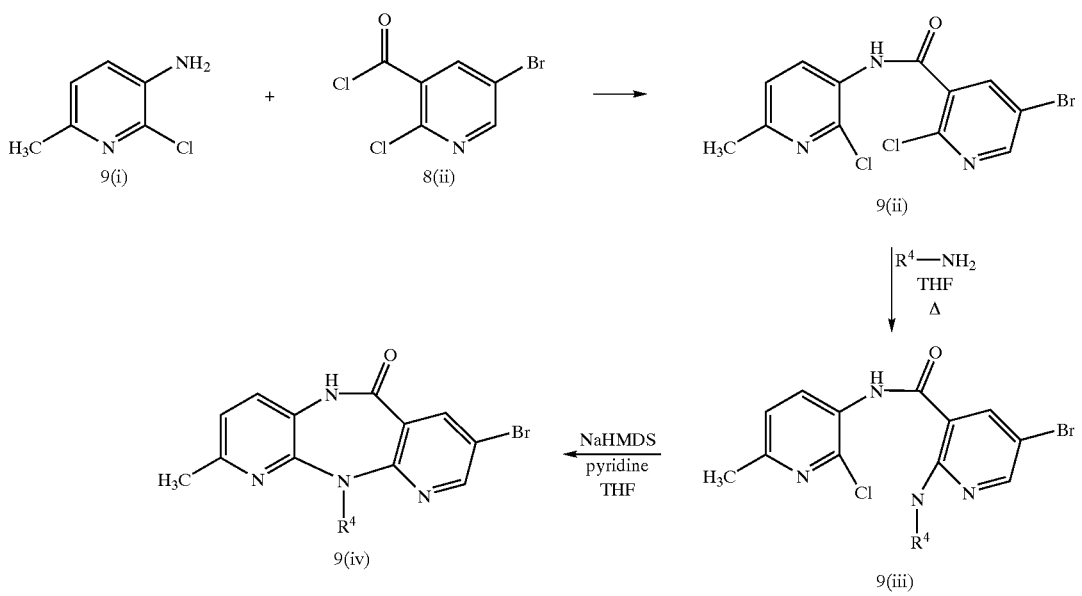

Scheme 9: Preparation of intermediates in which R¹ is Me

As stated before, the compounds provided by the invention inhibit the enzymatic activity of HIV-1 RT. Based upon testing of these compounds, as described below, it is known that they inhibit the RNA-dependent DNA polymerase activity of HIV-1 RT. One of skill in the art will also recognize that compounds of the invention may also inhibit the DNA-dependent DNA polymerase activity of HIV-1 RT. Using the Reverse Transcriptase (RT) Assay described below, compounds can be tested for their ability to inhibit the RNA-dependent DNA polymerase activity of HIV-1 RT. The specific compounds described in the Examples, which appear below, were so tested. The results of this testing appear in Table 9, as $1C_{50}(nM)$ and $EC_{50}$ (nM).

EXAMPLES

EXAMPLES

The present invention is illustrated in further detail by the following non-limiting examples. All reactions were performed in a nitrogen or argon atmosphere. Temperatures are given in degrees Celsius. Solution percentages or ratios express a volume to volume relationship, unless stated otherwise.

Abbreviations or symbols used herein include:
DEAD: diethyl azodicarboxylate;
DIAD: diisopropyl azodicarboxylate
DIEA: diisopropylethylamine;
DMAP: 4-(dimethylamino) pyridine;
DMSO: dimethylsulfoxide; 4
DMF: dimethylformamide;
ES MS: electron spray mass spectrometry;
Et: ethyl;
EtOAc: ethyl acetate;
$Et_2O$: diethyl ether;
HPLC: high performance liquid chromatography;
$^i$Pr: isopropyl
Me: methyl;
MeOH: methanol;
MeCN: acetonitrile;
NBS: N-bromosuccinimide
Ph: phenyl;
TBE: tris-borate-EDTA;
TBTU: 2-(1H-benzotriazol-1-yl)-N,N,N',N'-tetramethyluronium tetrafluoroborate;
TFA: trifluoroacetic acid;
THF: tetrahydrofuran;
MS (ES): electrospray mass spectrometry;
MS (FAB) or FAB/MS: fast atom bombardment mass spectrometry;
HRMS: high-resolution mass spectrometry;
PFU: plaque-forming units;
DEPC: diethyl pyrocarbonate;
DMSO: dimethylsulphoxide
DTT: dithiothreitol EDTA: ethylenediaminetetraacetate
UMP: uridine 5'-monophosphate
UTP: uridine 5'-triphosphate.
Syntheses The following examples illustrate methods for preparing compounds of the invention.

Example 1

Compound 122 and 101

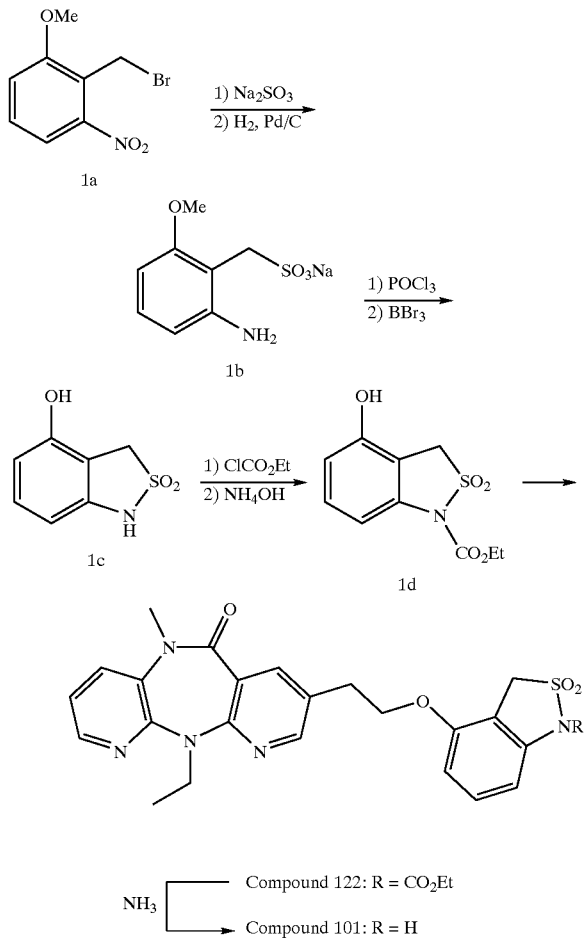

a) Sodium (2-Amino-6-methoxyphenyl)-methanesulfonate (1b)

A solution of sodium sulfite (0.36 g, 3.36 mmol) in water (10 mL) was added to a solution of 2-bromomethyl-1-methoxy-3-nitrobenzene (1) (Beckett, A. H.; Daisley, R. W.; Walker, J. Tetrahedron 1968, 24, 6093) (750 mg, 3.05 mmol) in acetone (5 mL). The solution was then stirred at reflux for 16 hours, cooled to ambient temperature and concentrated in vacuo. The resulting paste was dissolved in hot ethanol and filtered while hot. The mother liquor was cooled in an ice bath and the solid that precipitated was collected via suction filtration and dried in vacuo to give a white solid (1.10 g) containing the desired product and NaBr. A portion of this solid (100 mg, 0.41 mmol) was dissolved in 50% EtOH in $H_2O$ (5 mL), 10% Palladium on Carbon (10 mg) was added and the resulting mixture was stirred under an atmosphere of hydrogen until the reaction was judged to be complete by HPLC (90 minutes). The mixture was diluted with $H_2O$ (5 mL), filtered and concentrated to give aniline 1b (86 mg, 97% yield).

b) 2,2-Dioxo-2,3-dihydro-1H-2$\lambda^6$-benzo[c]isothiazol4-ol (1c)

Aniline 1b (35 mg, 0.16 mmol) was refluxed in $POCl_3$ (3.0 mL) for two hours. The reaction was cooled to room temperature and concentrated in vacuo. A mixture of ice and water was added carefully and the solution was made basic with 2N NaOH. The mixture was heated to 70° C. for 10 minutes and filtered while hot. The filtrate was acidified with concentrated HCl while cooled in an ice bath. The product which precipitated was collected via suction filtration to give the desired sultam (19 mg, 60%).

A solution of this product (0.8 g, 4.0 mmol) in $CH_2Cl_2$ (15 mL) was cooled to –78° C. A 3.3 M solution of $BBr_3$ in $CH_2Cl_2$ (7.9 mL, 32.3 mmol) was then added slowly over 15 minutes. After the addition was complete, the reaction mixture was allowed to warm to room temperature over four hours, then cautiously poured onto a mixture of ice and water. The mixture was extracted with EtOAc. The combined organic phases were washed with $H_2O$ and brine, dried over $MgSO_4$, filtered and concentrated in vacuo. The resulting solid was further purified by flash chromatography (50% EtOAc in hexanes) to give sultam phenol 1c (0.55 g, 74%).

c) 4-Hydroxy-2,2-dioxo-2,3-dihydro-2$\lambda^6$-benzo[c]isothiazole-1-carboxylic acid ethyl ester (1d)

Sultam 1c (100 mg, 0.54 mmol) was dissolved in pyridine (2.5 mL) and cooled to 0° C. Ethyl chloroformate (62 µL, 0.65 mmol) was added and the solution was warmed to room temperature and allowed to age for 16 hours. The pyridine was removed in vacuo and the reaction mixture was diluted with EtOAc, washed twice with 1.0 N HCl, once with water and once with brine. The solution was then dried over $MgSO_4$, filtered and the solvent removed in vacuo. Purification via flash chromatography gave the desired phenol 1d (37 mg, 27%).

Alternatively a solution of sultam 1c (1.75 g, 9.45 mmol) and $Et_3N$ (5.27 mL, 37.8 mmol) in THF (60 mL) was treated with ethyl chloroformate (2.71 mL, 28.3 mmol) over 10 minutes at 0° C. The resulting suspension was stirred at ambient temperature for two hours. Water was then introduced and the mixture was extracted with EtOAc. Washing the organic phase with 1.0 N HCl, $NaHCO_3$ and brine was followed by drying over $MgSO_4$. A beige solid (2.54 g, 86%) was obtained after removal of the solvent. To this solid (2.52 g, 8.04 mmol) in 25% EtOH in THF (80 mL) was added $NH_4OH$ (23 mL of 28% solution, 150 mmol) and the resulting solution was stirred for 90 minutes. The solvent was removed in vacuo and the product purified by flash chromatography (30% EtOAc in hexanes) to give 1d (1.41 g, 68%).

d) Compound 122

To a solution of phenol 1d (36 mg, 0.14 mmol), $PPh_3$ (74 mg, 0.28 mmol) and 5,11-dihydro-11-ethyl-8-(2-hydroxyethyl)-5-methyl-6H-dipyrido[3,2-b:2',3'-e][1,4]diazepin-6-one (42 mg, 0.14 mmol) in THF (2.5 mL) was slowly added DEAD (44 µL, 0.28 mmol) dropwise over 10 minutes. The resulting solution was stirred for 16 hours at ambient temperature. The reaction mixture was concentrated and purified by flash chromatography (60 to 80% EtOAc in hexanes) to give compound 122 (36 mg, 48 e) Compound 101

To a solution of compound 122 (25 mg, 0.047 mmol) in THF (1.5 mL) was added a 2 M solution of ammonia in EtOH (3.0 mL). The reaction was stirred for 16 hours and concentrated in vacuo. The mixture was diluted with EtOAc, washed twice with 1.0 N HCl, once with water, once with brine and dried over $MgSO_4$. Filtration and removal of solvent was followed by flash chromatography (50% EtOAc in hexanes) to give compound 101 (8 mg, 37%).

Example 2

Compound 402

This compound was prepared from 5,11-dihydro-11-ethyl-8-(2-hydroxyethyl)-5-methyl-6H-dipyrido[3,2-b:2',3'-e][1,4]diazepin-6-one and 5-hydroxy-2,2-dioxo-2,3-dihydro-2λ$^6$-benzo[c]isothiazole-1-carboxylic acid ethyl ester (prepared from 2-bromomethyl-4-methoxy-1-nitrobenzene (Beckett, A. H.; Daisley, R. W.; Walker, J. *Tetrahedron* 1968, 24, 6093) using a procedure similar to that described for 1d) using a procedure similar to that described above for compound 101.

Compounds 103, 104, 105, 106, 109, 110, 404, and 120: were prepared from 5,11-dihydro-11-ethyl-8-(2-hydroxyethyl)-4-methyl-6H-dipyrido[3,2-b:2',3'-e][1,4]diazepin-6-one and phenol 1d using a procedure similar to that described above for compound 101.

Example 3

Compounds 107 and 108

A 1 M solution of NaHMDS in THF (55 µL, 0.055 mmol) was added to a solution of compound 104 (25 mg, 0.053 mmol) in DMF (1 mL). The resulting solution was stirred briefly, then excess MeI was added, and stirring was continued for an additional 30 minutes. Water was added and the mixture was extracted with EtOAc. The combined organic extracts were washed with water and brine and dried over MgSO$_4$. Flash chromatography (50% EtOAc in hexanes) followed by preparative HPCL using a gradient of MeCN/H$_2$O containing TFA (0.06%) (CombiPrep ODS-AQ 50×20 mm, 5µ, 120 Å) gave compound 107 (4.7 mg, 18%) and compound 108 (2.9 mg, 11%).

Example 4

Compound 111

A mixture of compound 103 (18 mg, 0.037 mmol), K$_2$CO$_3$ (57 mg, 0.41 mmol) and MeI (0.1 mL) in DMF (0.5 mL) was stirred for 48 hours. The mixture was diluted with EtOAc and washed twice with water, once with brine and was dried over MgSO$_4$. Flash chromatography (50% EtOAc in hexanes) gave compound 111 which was lyophilized from a mixture of CH$_3$CN and water to give a white solid (10 mg, 54%).

Compounds 112, 116, 117, 118, 119 and 121 were prepared using a procedure similar to that described above for compound 111.

Example 5

Compounds 301 and 303

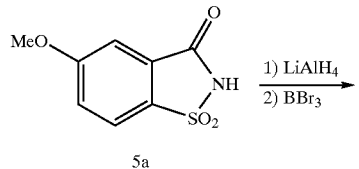

5a

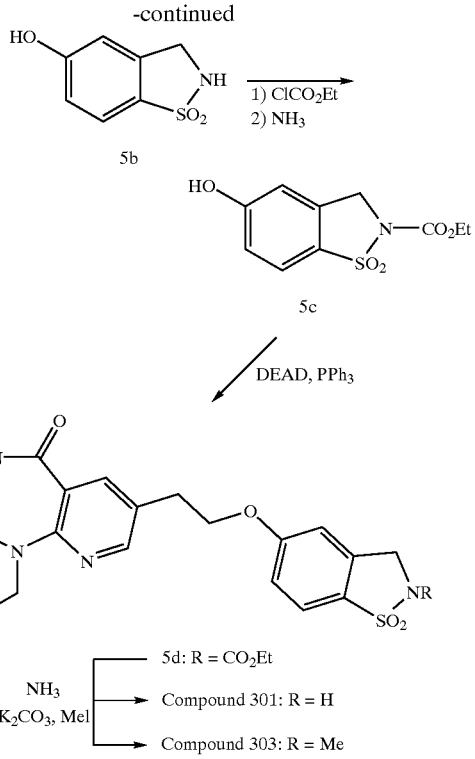

a) 1,1-Dioxo-2,3-dihydro-1H-1λ$^6$-benzo[d]isothiazol-5-ol (5b)

5-Methoxy-1,1-dioxo-1,2-dihydro-1λ$^6$-benzo[d]isothiazol-3-one 5a (Lomardino, J. G. *J. Org. Chem.* 1971, 1843) (1.50 g, 7.04 mmol) was dissolved in THF (75 mL) and LiAlH$_4$ (35.2 mL of a 1.0 M solution in THF, 35.2 mmol) was introduced. The resulting solution was stirred at ambient temperature for 16 hours. The reaction mixture was carefully quenched with a saturated solution of Rochelle's salt, diluted with EtOAc and stirred vigorously for 20 minutes. Filtration through Celite® was followed by concentrated in vacuo. The residue was purified by flash chromatography (70 to 80% EtOAc in hexanes) to give a white solid (0.46 g, 33%). This solid (0.38 g, 1.91 mmol) was dissolved in CH$_2$Cl$_2$ (10 mL) and the solution was cooled to −78° C. BBr$_3$ (5.46 mL of a 3.5 M solution in CH$_2$Cl$_2$, 19.1 mmol) was added, the cold bath was removed and the resulting mixture was aged for 16 hours. The reaction was quenched by careful addition of H$_2$O, extracted with EtOAc and the organic extracts were dried over MgSO$_4$. Purification by flash chromatography (70 to 80% EtOAc in hexanes) gave the desired material 5b (135 mg, 38%).

b) 5-Hydroxy-1,1-dioxo-1,3-dihydro-1λ$^6$-benzo[d]isothiazole-2-carboxylic acid ethyl ester (5c)

To sultam 5b (0.10 g, 0.54 mmol) dissolved in pyridine (5.0 mL) was added ethyl chloroformate (0.51 mL, 5.38 mmol). The reaction was stirred for 16 hours at room temperature then concentrated in vacuo. The mixture was extracted with EtOAc, washed twice with 1.0 N HCl, once with water, once with saturated NaHCO$_3$, once with brine and was dried over MgSO$_4$. Purification by flash chromatography (50% EtOAc in hexanes) gave the bis carbamate (96 mg, 54%). This material (63 mg, 0.19 mmol) was dissolved in 10% EtOH in EtOAc (10 mL), a 2.0 M solution of NH$_3$ in EtOH (1.91 mL, 3.83 mmol) was added and the solution stirred for one hour at ambient temperature. The reaction mixture was concentrated and purified by flash chromatography (50% EtOAc in hexanes) to give carbamate 5c (42 mg, 68%).

c) Compound 301

Carbamate 5c (36 mg, 0.14 mmol), PPh₃ (72 mg, 0.27 mmol) and 5,11-dihydro-11-ethyl-8-(2-hydroxyethyl)-5-methyl-6H-dipyrido[3,2-b:2',3'-e][1,4]diazepin-6-one (41 mg, 0.14 mmol) were dissolved in THF (2.5 mL). DEAD (43 μL, 0.27 mmol) was added slowly and the resulting solution was aged for 18 hours. The reaction mixture was diluted with EtOAc, washed twice with water, dried over MgSO₄, filtered and concentrated in vacuo. The resulting mixture was partially purified by flash chromatography (70 to 80% EtOAc in hexanes) to give 132 mg of adduct 5d (contaminated with triphenylphosphine oxide). This material was dissolved in 5:1 EtOH:THF (6 mL) and a 2.0 M solution of NH₃ in EtOH (6.15 mL, 12.2 mmol) was added. After stirring for 16 hours, the reaction was diluted with EtOAc and extracted thrice with 1.0N NaOH. The aqueous phase was acidified with concentrated HCl and extracted three times with EtOAc. After drying over MgSO₄ the concentrated residue was purified by flash chromatography (70 to 80% EtOAc in hexanes) to give derivative compound 301 (18 mg, 16%).

d) Compound 303

A mixture of compound 301 (8.7 mg, 0.02 mmol), K₂CO₃ (10 mg, 0.07 mmol) and MeI (3.5 μL, 0.06 mmol) in DMF was stirred at room temperature. After 2 days additional, K₂CO₃ (20 mg) and MeI (50 μL) were added and stirring continued overnight. The mixture was filtered and the filtrate was concentrated. Preparative TLC (60% EtOAC in hexanes) gave the desired material (6.2 mg, 69%) which was lyophilized from a mixture of CH₃CN and water.

Compounds 202, 310 and 223 were prepared using a procedure similar to that described above for compound 301.

Example 6

Compounds 306 and 307

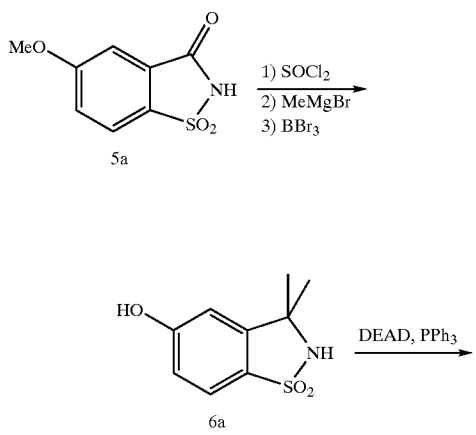

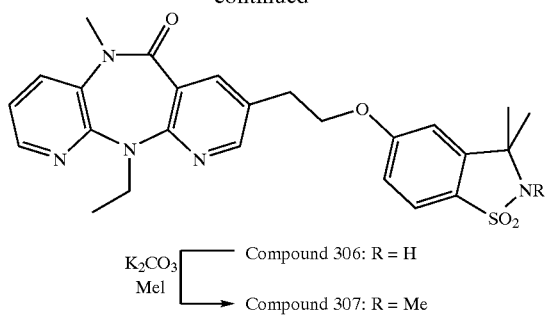

a) 3,3-Dimethyl-1,1-dioxo-2,3-dihydro-1H-1λ⁶-benzo[d]isothiazol-5-ol (6a)

Saccharine 5a (290 mg, 4.08 mmol) was dissolved in xylenes (10 mL) containing a small amount of activated charcoal (50 mg). DMF (2 drops) and freshly distilled SOCl₂ (0.30 mL, 4.08 mmol) were added and the resulting mixture was heated to reflux for 15 hours. The solution was then cooled to room temperature and concentrated in vacuo to give a paste. The paste was dissolved in THF and the resulting solution was then added dropwise to a solution of MeMgCl (1.36 mL of a 3.0 M solution in THF, 4.08 mmol) in THF (7 mL). The resulting solution was stirred at 40° C. for 24 hours. After removal of solvent, the desired compound (124 mg, 40%) was obtained by flash chromatography (40 to 60% EtOAc in hexanes). To a solution of this material (100 mg, 0.44 mmol) in CH₂Cl₂ (50 mL) at −78° C. was added a 1.0 M solution of BBr₃ (2.64 mL, 2.64 mmol) in CH₂Cl₂. The resulting mixture was stirred for 16 hours at ambient temperature. Careful quenching by the addition of H₂O was followed by extraction with EtOAc. The combined organic extracts were washed with water and brine then dried over MgSO₄. Compound 6a (54 mg, 58%) was delivered by flash chromatography (40 to 60% EtOAc in hexanes).

b) Compound 306

To a solution of sultam 6a (50 mg, 0.24 mmol), PPh₃ (123 mg, 0.47 mmol) and 5,11-dihydro-11-ethyl-8-(2-hydroxyethyl)-5-methyl-6H-dipyrido[3,2-b:2',3'-e][1,4]diazepin-6-one (70 mg, 0.24 mmol) in THF (2.5 mL) was slowly added DEAD (0.074 mL, 0.470 mmol). After stirring for three hours, the solvent was removed in vacuo and the product was purified by flash chromatography (60 to 80% EtOAc in hexanes). Lyophilization from CH₃CN/H₂O gave the desired adduct compound 306 (67 mg, 58%) as a white solid.

c) Compound 307

A mixture of compound 306 (10 mg, 0.02 mmol), K₂CO₃ (100 mg, 0.72 mmol) and MeI (0.10 mL, 1.13 mmol) in THF (1.0 mL) was stirred vigorously for 96 hours. After dilution with EtOAc, the mixture was washed with water and dried over MgSO₄. Flash chromatography (80% EtOAc in hexanes) gave compound 307 (9 mg, 89%).

Compounds 409 and 311 were prepared using a procedure similar to that described above for compound 306.

Example 7

Compound 803

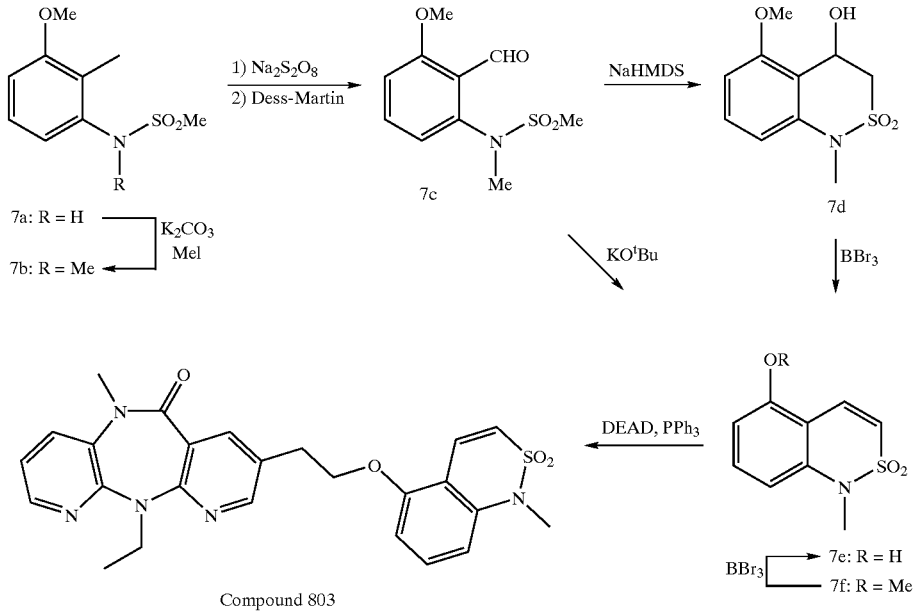

a) N-(3-Methoxy-2-methylphenyl)-N-methylmethanesulfonamide (7b)

A slurry of N-(3-methoxy-2-methylphenyl)methanesulfonamide 7a (Blondet, D.; Pascal, J. -C. *Tetrahedron Lett.* 1994, 35, 2911) (4.5 g, 20.9 mmol), $K_2CO_3$ (4.33 g, 31.4 mmol) and MeI (6.52 mL, 105 mmol) in DMF (100 mL) was stirred vigorously for 5 days. The reaction was poured onto $H_2O$ (250 mL), stirred for 10 minutes and then extracted with ether. The combined organic extracts were washed with water and brine and dried over $MgSO_4$ to give 7b (5.10 g) after removal of the solvent.

b) N-(2-Formyl-3-methoxyphenyl)-N-methylmethanesulfonamide (7c)

A solution of 7b (1.0 g, 4.37 mmol) in $CH_3CN$ (15 mL) was added to a solution of $K_2S_2O_8$ (2.35 g, 8.73 mmol) and $CuSO_4$ (219 mg, 0.87 mmol) in $H_2O$ (15 mL). Pyridine (0.71 mL, 8.73 mmol) was introduced and the resulting mixture was stirred vigorously at reflux for two hours. After cooling to room temperature, the suspension was filtered. The filtrate was extracted with EtOAc and the extracts were washed with 1.0 N NaOH, 1.0 N HCl, water and brine then dried over $MgSO_4$. A syrup (731 mg) was obtained after removal of the solvent. This syrup (731 mg) was dissolved in $CH_2Cl_2$ (15 mL) containing water (two drops). Dess-Martin periodinane (1.69 g, 3.83 mmol) was added and the resulting solution was stirred for 90 minutes. A mixture of equal parts of a 10% $Na_2S_2O_3$ solution and a saturated $NaHCO_3$ solution was added and the resulting two phase mixture was stirred until both layers were clear.

The mixture was extracted with EtOAc and the combined organic extracts were washed with saturated $NaHCO_3$, water and brine then dried over $MgSO_4$. After being stripped of solvent compound 7c (432 mg, 56%) was obtained by flash chromatography (40 to 70% EtOAc in hexanes).

c) 1-Methyl-2,2-dioxo-1,2-dihydro-2$\lambda^6$-benzo[c][1,2]thiazin-5-ol (7f)

A solution of aldehyde 7c (400 mg, 1.65 mmol) in THF (200 mL) was treated with NaHMDS (2.88 mL of a 1.0 M solution in THF, 2.88 mmol) at 0° C. over 10 minutes. The resulting solution was stirred for one hour at that temperature. The reaction was quenched by the addition of saturated $NH_4Cl$ and extracted with EtOAc. The combined organic phases were washed with water and brine then dried over $MgSO_4$. Purification by flash chromatography (40–60% EtOAc in hexanes) gave 7d (172 mg, 43%). To a solution of this material (120 mg, 0.49 mmol) in $CH_2Cl_2$ (15 mL) was added $BBr_3$ (3.95 mL of a 1.0 M solution in $CH_2Cl_2$, 3.95 mmol) at 0° C. The cold bath was then removed and the resulting solution was stirred for 16 hours at ambient temperature. The reaction was carefully quenched by the addition of $H_2O$ and extracted with EtOAc. The combined extracts were washed with water and brine then dried over $MgSO_4$. Compound 7f (76 mg, 73%) was obtained after flash chromatography (30 to 100% EtOAc in hexanes).

Alternatively KOtBu (1.92 g, 17.1 mmol) was added in two portions to a solution of aldehyde 7c (3.80 g, 15.6 mmol) in THF (300 mL) over 10 minutes. The reaction was allowed to stir for 10 minutes at ambient temperature then was quenched by the addition of $H_2O$. Extraction with $CH_2Cl_2$ was followed by washing with water and brine. After being dried over $MgSO_4$, the solution was filtered and the product stripped of solvent. Purification by flash chromatography (70 to 80% EtOAc in hexanes) gave 7e (2.97 g, 85%). This compound was converted to 7f using a procedure similar to that described above for 7d.

d) Compound 803

To a solution of sultam 7f (49 mg, 0.23 mmol), $PPh_3$ (122 mg, 0.46 mmol) and 5,11-dihydro-11-ethyl-8-(2-hydroxyethyl)-5-methyl-6H-dipyrido[3,2-b:2',3'-e][1,4]diazepin-6-one (70 mg, 0.23 mmol) in THF (3.0 mL) was slowly added DEAD (73 μL, 0.46 mmol) at 0° C. The resulting solution was aged for 15 minutes at 0° C. and for 30 minutes at ambient temperature. Flash chromatography (60 to 100% EtOAc in hexanes) gave compound 803 (24 mg, 17%).

Compound 804 was prepared using a procedure similar to that described above for compound 803.

Example 8

Compound 113

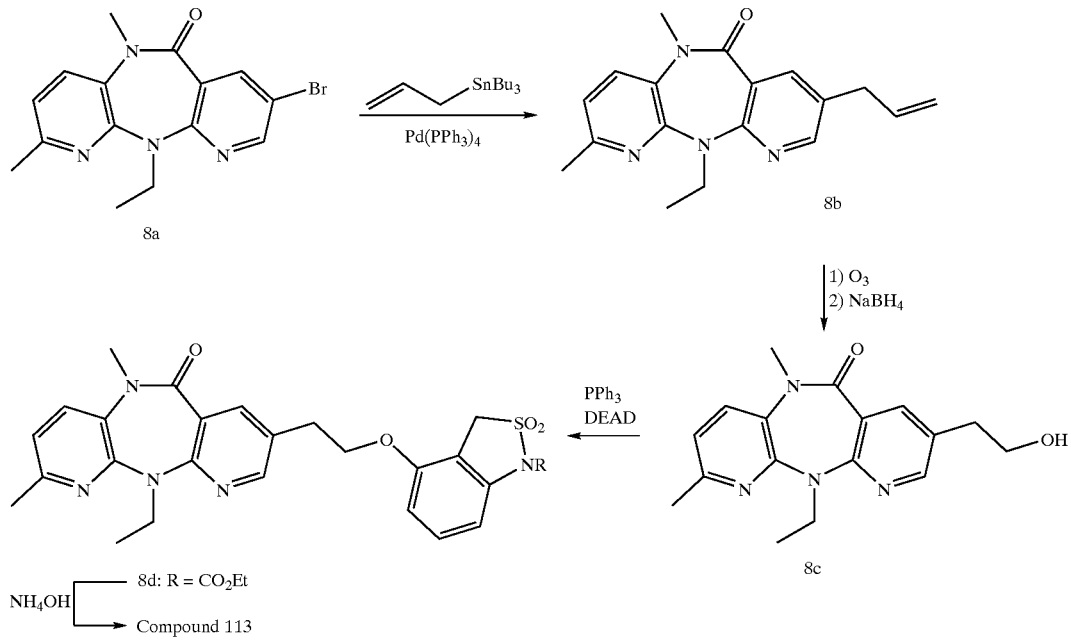

a) A mixture of bromide 8a (Cywin, C. L.; Klunder, J. M.; Hoermann, M.; Brickwood, J. R.; David, E.; Grob, P. M.; Schwartz, R.; Pauletti, D.; Barringer, K. J.; Shih, C. -K.; Sorge, P. M.; Erickson, D. A.; Joseph, D. P.; Hattox, S. E. *J. Med. Chem.*, 1998, 41, 2972) (3.5 g, 10 mmol), allyltributyltin (3.72 mL, 12 mmol) and Pd(PPh$_3$)$_4$ (1.16 g, 1 mmol) in DMF (30 mL) was stirred at 80° C. for 2.5 hours. The DMF was the removed in vacuo and the residue subjected to flash chromatography (20% EtOAc in hexanes) to give 8b (2.32 g, 75%).
b) Allyl adduct 8b (2.32 g, 7.52 mmol) was dissolved in a mixture of equal parts CH$_2$Cl$_2$ and methanol (200 mL) and the resulting solution was cooled to −78° C. The solution was sparged with ozone for 30 minutes, oxygen for 10 minutes and nitrogen for 15 minutes. NaBH$_4$ (567 mg, 15 mmol) was then added at −78° C. and the resulting solution was stirred at that temperature for 15 minutes and at room temperature for 3 hours. A saturated solution of NH$_4$Cl (100 mL) was then added and stirring was continued briefly. The organic solvents were removed under reduced pressure and the residue was extracted with EtOAc. The combined organic phases were washed with water and brine then dried over MgSO$_4$. Purification by flash chromatography (80% EtOAc in hexanes) gave the desired alcohol (1.90 g, 81%).
d) To a solution of 8c (100 mg, 0.32 mmol), PPh$_3$ (126 mg, 0.48 mmol) and phenol 1d (123 mg, 0.48 mmol) in THF (1 mL) was added DIAD (94 μL, 0.48 mmol) over a period of one hour. After two additional hours of stirring the solvent was removed and the residue flash chromatographed (50% EtOAc in hexanes) to give adduct 8d (162 mg, 92%).
e) Compound 113

Carbamate 8d (162 mg, 0.29 mmol) was dissolved in a 3:1 mixture of THF and EtOH to which NH$_4$OH was added (1.5 mL). The mixture was stirred at room temperature for 20 hours and was then concentrated. The residue was dissolved in EtOAc and was washed with 1 N HCl. Treatment with MgSO$_4$ was followed by flash chromatography (50% EtOAc in hexanes) to deliver compound 113 (125 mg, 90%)

Example 9

Compound 114

This compound was prepared from compound 113 using a procedure similar to that described above for compound 303.

Example 10

Compound 115

This compound was prepared from compound 113 using a procedure similar to that described above for compound 111 using EtI in place of MeI.

Example 11

Compound 601

To a solution of 5,11-dihydro-11-ethyl-8-(2-hydroxyethyl)-5-methyl-6H-dipyrido[3,2-b:2',3'-e][1,4]diazepin-6-one (30 mg, 0.10 mmol), 1-benzyl-2,2-dioxo-1,2,3,4-tetrahydro-2-benzo[c][1,2]thiazin-5-ol (Blondet, D.; Pascal, J. -C. *Tetrahedron Lett.* 1994, 35, 2911) (38 mg, 0.13 mmol) and PPh$_3$ (39 mg, 0.15 mmol) in THF (2 mL) was added slowly DEAD (0.03 mL, 0.15 mmol). The resulting solution was stirred at room temperature for 2 h at which time the reaction was judged complete by TLC analysis. Evaporation of the solvent followed by flash chromatography gave the desired adduct (29.9 mg, 41%). This compound was dissolved in EtOAc (1 mL) and EtOH (1 mL). Pd(OH)$_2$ was added and the resulting suspension was stirred under an atmosphere of hydrogen for 5 days. The catalyst was removed by filtration through a glass microfibre and the filtrate was concentrated in vacuo. Flash chromatography (50% EtOAc in hexanes) followed by preparative TLC (60% EtOAc in hexanes, 2× elution) gave the compound 601 (9.6 mg, 38%) which was lyophilized from CH$_3$CN and water.

Compound 602 was prepared using a procedure similar to that described above for compound 601.

Compound 223 was prepared using a procedure similar to that described above for compound 301.

Example 12

Compounds 505 and 508

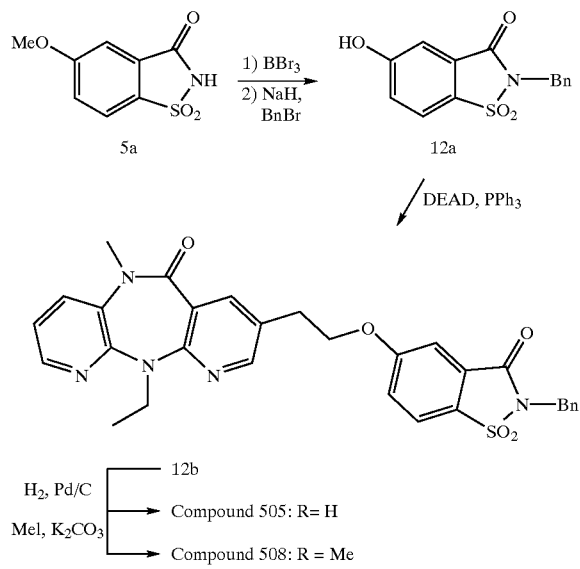

a) 2-Benzyl-5-hydroxy-1,1-dioxo-1,2-dihydro-1 k-benzo[d]isothiazol-3-one (12a)

A slurry of saccharine 5a (290 mg, 1.36 mmol) in $CH_2Cl_2$ (25 mL) was cooled to −78° C. and a 1.0 M solution of $BBr_3$ in $CH_2Cl_2$ (8.17 mL, 8.17 mmol) was added. The cold bath was removed and the reaction was aged for 16 hours during which time the reaction warmed to ambient temperature. The reaction was carefully quenched with $H_2O$ and extracted three times with EtOAc. The combined extracts were dried over $MgSO_4$, filtered and concentrated to give a white solid (273 mg, 100%). This material (500 mg, 2.51 mmol) was dissolved in 10:3 THF:DMF (13 mL) and NaH (63 mg, 2.63 mmol) was added. The resulting mixture was stirred for 15 minutes after which time benzyl bromide (0.30 mL, 2.51 mmol) was introduced and the resulting mixture was further stirred for 16 hours. The solution was poured carefully into 1.0 N HCl and extracted with $Et_2O$. The combined organic extracts were washed with water and brine and dried over $MgSO_4$. The resulting crude material was purified by flash chromatography (30 to 50% EtOAc in hexanes) to give the desired 12a (140 mg, 20%).

b) Phenol 12a (100 mg, 0.35 mmol), $PPh_3$ (182 mg, 0.69 mmol) and 5,11-dihydro-11-ethyl-8-(2-hydroxyethyl)-5-methyl-6H-dipyrido[3,2-b:2',3'-e][1,4]diazepin-6-one (103 mg, 0.35 mmol) were dissolved in THF (5.0 mL). To this solution was added DEAD (110 μL, 0.69 mmol) dropwise over 15 minutes. The resulting solution was aged for three hours. The solvent was removed in vacuo and the residue was purified by flash chromatography (70 to 100% EtOAc in hexanes) to give adduct 12b (154 mg, 78%).

c) Compound 505

Benzyl saccharine 12b (50 mg, 0.09 mmol) was dissolved in 2:1 THF:EtOH (3.0 mL) containing 10% Palladium on carbon (35 mg) and the resulting mixture was stirred under an atmosphere of hydrogen for 16 hours. The suspension was filtered, and the filtrate was concentrated. The solid so obtained was purified by trituration with EtOAc to give product compound 505 (9 mg, 21%).

d) Compound 508

To a slurry of compound 505 (20 mg, 0.042 mmol) in THF (5.0 mL) was added 0.8 M $CH_2N_2$ solution in $Et_2O$ (1.5 mL). The solution was then stirred for one hour during which time dissolution occurred. After removal of solvent, the compound was purified by flash chromatography (50 to 70% EtOAc in hexanes) and the residue so obtained was lyophilized from $CH_3CN/H_2O$ to give compound 508 (14.4 mg, 70%).

Reverse Transcriptase (RT) Assays

Assay Theory

Among the enzymes for which Human Immunodeficiency Virus (HIV-1) encodes is a reverse transcriptase (1), so-named because it transcribes a DNA copy from an RNA template. This activity can be quantitatively measured in a cell-free enzyme assay, which has been previously described (2), and is based upon the observation that reverse transcriptase is able to use a synthetic template poly r(C) primed with oligo d(G) to transcribe a radio-labelled, acid-precipitable DNA strand utilising $^3$H-dGTP as a substrate. The assay described below utilises the wild type (WT) enzyme, which is the predominant form of the enzyme observed with patients infected with HIV-1. Utilisation of mutant RT enzymes (for example, Y181C, prepared by site-directed mutagenesis in which the tyrosine residue at codon 181 has been replaced by a cysteine residue, or the mutants K103N, V106A and Y188C) and analogous assay conditions allows compounds to be evaluated for their effectiveness at inhibiting the mutant enzymes.

Materials

Preparation of the Enzyme

The HIV-1 RT expression clone, pKRT2, was obtained from Yale University (3). An overnight culture, grown in 2×YT medium (37° C., 225 rpm) (4), supplemented with 100 μg/mL ampicillin for positive selection was used to inoculate the 2×YT medium. The culture was incubated (37° C., 225 rpm) until it reached an OD600 of 0.6–0.9. At that time, the repressor inhibitor IPTG (isopropyl P-D-thiogalactopyranoside) was added to 0.5 mM, and the mixture was incubated for an additional 2 hours.

Purification of Enzyme

Purification of recombinant reverse transcriptase was performed using a combination of methods previously described (5). This procedure is summarised briefly as follows: E. Coli containing RT-1 wt or RT-1 (Y181 C) were suspended in 50 mM MES, pH 6.0 containing 10% glycerol, lysed in a French press, centrifuged, and the supernates discarded. Lysate pellets were extracted with buffer A (50 mM MES, pH 6.0, 100 mM KCl, 50 mM KPi, 10% glycerol, 0.02% hexyl-β-glucoside), and re-centrifuged; nucleic acid in supernates was precipitated with 0.1% polyethylenimine. Clarified extracts were chromatographed on hydroxylapatite (BioRad BioGel HT) using a gradient of 0–0.25M KPi in buffer A. Fractions containing RT were pooled, diluted with an equal volume of buffer B (50 mM Bis-tris propane, pH 7.0, 100 mM $(NH_4)_2SO_4$, 10% glycerol), and loaded onto a Heparin-Sepharose CL-6B (Pharmacia) column. Bound RT was eluted with a gradient of 0 to 1.0M $(NH_4)_2$ $SO_4$ in buffer B. Heparin-Sepharose fractions containing RT were concentrated (Amicon YM-30 membrane), combined with equal volumes of 2.0M $(NH_4)_2SO_4$ in buffer B and injected onto a 21.5.times.150 mm TSK Phenyl-5PW HIC HPLC column (Phenomenex). Heterodimeric RT was eluted using a descending gradient of 1.0M to 0M $(NH_4)_2SO_4$ in buffer B, concentrated, and stored at 4° C.

The products were 98% pure by SDS-PAGE and had near equivalent specific activities of about 20 nmol dGTP/mg/min at 25° C.

c) Composition of Stock and Reaction Mixture

| Stock reagent concentrations | 2.4× mix concentration | Final assay |
|---|---|---|
| 1M Tris pH 7.8 | 120 mM | 50 mM |
| 1M Dithiothreitol | 9.6 mM | 4 mM |
| 1M NaCl | 144 mM | 60 mM |
| 1M MgCl$_2$ | 4.8 mM | 2.0 mM |
| [poly r(C)$_{500}$/oligo d(G)$_{10}$] (27:1) | 11.6 μg/mL | 4.8 μg/mL |
| $^3$H-dGTP (93 [2M, 10.7 Ci/mmol) | 1. μM | 0.45 μM |
| Chaps | — | 0.02% |
| RT enzyme | — | 0.02% |
| RT enzyme | — | 0.63 nM |
| Test Compound | — | 10 μg/mL |

Assay Procedure

The 2.4× concentrated stock reaction mixture was aliquoted and stored at −20° C. The mixture is stable and can be thawed for use in each assay. This enzyme assay has been adapted to a 96 well microtiter plate system, and has been previously described (6). Tris buffer (50 mM, pH 7.8), vehicle (solvent diluted to match the compound dilution), or compounds in vehicle were dispensed into 96-well microtiter plates (10 μL/well; 3 wells/compound). The HIV-1 RT enzyme was thawed, diluted in 50 mM Tris pH 7.8 containing 0.05% Chaps to give 1.5 nM enzyme and 25 μL were dispensed per well. Ten μL of 0.5M EDTA were added to the first three wells of the microtiter plate. EDTA chelates the Mg$^{2+}$ present and prevents reverse transcription. This group served as background polymerisation, which was subtracted, from all other groups. Twenty-five μl of the 2.4× reaction mixture was added to all wells and the assay was allowed to incubate at room temperature for 30 minutes. The assay was terminated by precipitating the DNA in each well with 60 μL of sodium pyrophosphate (2% w/v) in 10% trichloroacetic acid (TCA) (10% w/v). The microtiter plate was incubated for 15 minutes at 4° C. and the precipitate was harvested onto #30 glass fibre paper (Schleicher & Schuell) using a Tomtech 96-well harvester. The filters were dried, placed in plastic bags with Betaplate scintillation cocktail (Pharmacia/LKB) and counted in the Betaplate counter (Pharmacia/LKB).

The calculation for percent inhibition is as follows:

$$\% \text{ inhibition} = \frac{[CPM \text{ mean test value} - CPM \text{ mean control value}]}{[CPM \text{ mean control value}]} \times 100$$

Using the above assay, compounds of the invention were tested for inhibition of RT wildtype (WT) and mutant enzymes. The results are listed in Table 9 as IC$_{50}$ (nM).

A similar assay may be used, in which the oligo d(G) primer is biotinylated. After incubation with the enzyme, biotinylated DNA is harvested using Strepavidin SPA beads. The beads are counted for radioactivity as detailed above.

In order to confirm that compounds, which are active in the RT Assay, also have the ability to inhibit HIV replication in a living system, compounds according to the invention were also tested in the human T-Cell Culture (Syncytia) Assay described below.

ELISA Assay for Assessment of Activity in Cell Culture

Compounds of the invention were tested for their ability to inhibit HIV replication in cell culture. Viruses coding for Wild type and mutant enzymes were used. T-lymphocytes were infected with the virus, infected cells were incubated in the presence of varying amounts of compounds of the invention, and an ELISA assay for the viral protein p24 was used to quantify viral replication. Table 9 lists the results as EC$_{50}$ (nM).

References (Incorporated Herein by Reference)

1. Benn, S., et al. Science 230:949, 1985.
2. Farmerie, W. G. et. al. Science 236:305, 1987.
3. D'Aquila, R. T. and Summers, W. C. J. Acq. 1 mm. Def. Syn. 2:579, 1989.
4. Maniatis, T, Fritsch, E. F., and J. Sambrook, Eds. Molecular Cloning: A Laboratory Manual, Cold Spring Harbor Laboratory, 1982.
5. a) Warren, T. C. et al. Protein Expression & Purification 3:479, 1992; b) Kohlstaedt, L. A. Science 256(5065): 1783, 1992.
6. Spira, T., et. al. J. Clinical Microbiology, 25:97, 198

TABLE 1

| Cmpd No. | R$^1$ | R$^2$ | R$^3$ | R$^4$ | R$^5$ | R$^{8a}$ | R$^{8b}$ | A | m/z (ES+) |
|---|---|---|---|---|---|---|---|---|---|
| 101 | H | H | CH$_3$ | CH$_3$CH$_2$ | H | H | H | CH$_2$CH$_2$ | 466 (MH), 488 (M + 23) |
| 103 | F | H | CH$_3$ | CH$_3$CH$_2$ | H | H | H | CH$_2$CH$_2$ | 484 (MH), 506 (M + 23) |
| 104 | F | H | CH$_3$ | CH$_3$CH$_2$ | H | H | H | CH$_2$ | 470 (MH) |
| 105 | H | H | CH$_3$ | cyclopropyl | H | H | H | CH$_2$CH$_2$ | 478 (MH), 500 (M + 23) |
| 106 | F | CH$_3$ | H | cyclopropyl | H | H | H | CH$_2$CH$_2$ | 496 (MH) |

TABLE 1-continued

| Cmpd No. | R¹ | R² | R³ | R⁴ | R⁵ | R⁸ᵃ | R⁸ᵇ | A | m/z (ES+) |
|---|---|---|---|---|---|---|---|---|---|
| 107 | F | H | $CH_3$ | $CH_3CH_2$ | $CH_3$ | H | H | $CH_2$ | 484 (MH), 506 (M + 23) |
| 108 | F | H | $CH_3$ | $CH_3CH_2$ | $CH_3$ | H | $CH_3$ | $CH_2$ | 498 (MH), 520 (M + 23) |
| 109 | $CH_3$ | $CH_3$ | H | $CH_3CH_2$ | H | H | H | $CH_2CH_2$ | 480 (MH), 502 (M + 23) |
| 110 | F | $CH_3$ | H | $CH_3CH_2$ | H | H | H | $CH_2CH_2$ | 484 (MH) |
| 111 | F | H | $CH_3$ | $CH_3CH_2$ | $CH_3$ | H | H | $CH_2CH_2$ | 498 (MH), 520 (M + 23) |
| 112 | F | $CH_3$ | H | $CH_3CH_2$ | $CH_3$ | H | H | $CH_2CH_2$ | 498 (MH) |
| 113 | $CH_3$ | H | $CH_3$ | $CH_3CH_2$ | H | H | H | $CH_2CH_2$ | 480 (MH) |
| 114 | $CH_3$ | H | $CH_3$ | $CH_3CH_2$ | $CH_3$ | H | H | $CH_2CH_2$ | 494 (MH) |
| 115 | $CH_3$ | H | $CH_3$ | $CH_3CH_2$ | $CH_2CH_3$ | H | H | $CH_2CH_2$ | 508 (MH) |
| 116 | H | H | $CH_3$ | cyclopropyl | $CH_3$ | H | H | $CH_2CH_2$ | 492 (MH), 514 (M + 23) |
| 117 | $CH_3$ | $CH_3$ | H | $CH_3CH_2$ | $CH_3$ | H | H | $CH_2CH_2$ | 494 (MH), 516 (M + 23) |
| 118 | F | $CH_3$ | H | cyclopropyl | $CH_3$ | H | H | $CH_2CH_2$ | 510 (MH) |
| 119 | F | $CH_3$ | $CH_3$ | cyclopropyl | $CH_3$ | H | H | $CH_2CH_2$ | 524 (MH) |
| 120 | H | $CH_3$ | H | $CH_3CH_2$ | H | H | H | $CH_2CH_2$ | 466 (MH) |
| 121 | H | $CH_3$ | H | $CH_3CH_2$ | 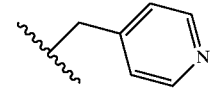 | H | H | $CH_2CH_2$ | 520 (MH) |
| 122 | H | H | $CH_3$ | $CH_3CH_2$ | $CO_2CH_2CH_3$ | H | H | $CH_2CH_2$ | 538 (MH) |
| 127 | H | H | $CH_3$ | $CH_3CH_2$ | $CH_2COOH$ | H | H | $CH_2CH_2$ | 524 (MH) |
| 128 | H | H | $CH_3$ | $CH_3CH_2$ | 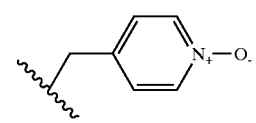 | H | H | $CH_2CH_2$ | 597 (MH) |
| 129 | H | H | $CH_3$ | $CH_3CH_2$ | $CH_2CH_2OH$ | H | H | $CH_2CH_2$ | 510 (MH) |
| 130 | H | H | $CH_3$ | $CH_3CH_2$ | 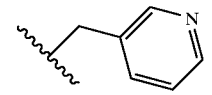 | H | H | $CH_2CH_2$ | 573 (MH) |
| 131 | H | H | $CH_3$ | $CH_3CH_2$ | 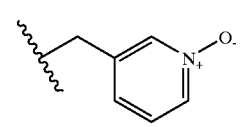 | H | H | $CH_2CH_2$ | 557 (MH) |
| 132 | H | H | $CH_3$ | $CH_3CH_2$ | 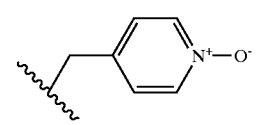 | H | H | $CH_2CH_2$ | 573 (MH) |
| 133 | H | H | $CH_3$ | $CH_3CH_2$ | $CH_2CONH-OH$ | H | H | $CH_2CH_2$ | 539 (MH) |
| 134 | H | H | $CH_3$ | $CH_3CH_2$ | $CH_2CON(CH_3)-OH$ | H | H | $CH_2CH_2$ | 553 (MH) |
| 135 | H | H | $CH_3$ | $CH_3CH_2$ | $(CH_2)_3COOCH_2CH_3$ | H | H | $CH_2CH_2$ | 580 (MH) |
| 136 | H | $CH_3$ | H | $CH_3CH_2$ | (see 130) | H | H | $CH_2CH_2$ | 573 (MH) |

TABLE 1-continued

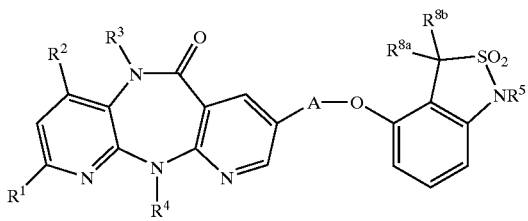

| Cmpd No. | $R^1$ | $R^2$ | $R^3$ | $R^4$ | $R^5$ | $R^{8a}$ | $R^{8b}$ | A | m/z (ES+) |
|---|---|---|---|---|---|---|---|---|---|
| 137 | H | $CH_3$ | H | $CH_3CH_2$ | 3-pyridyl N-oxide-methyl | H | H | $CH_2CH_2$ | 573 (MH) |
| 138 | H | H | $CH_3$ | $CH_3CH_2$ | $CH_2CH(CH_3)COOH$ | H | H | $CH_2CH_2$ | 552 (MH) |
| 139 | H | H | $CH_3$ | $CH_3CH_2$ | $CH_2CH_2C(O)NH$-cyclopropyl | H | H | $CH_2CH_2$ | 563 (MH) |
| 140 | H | H | $CH_3$ | $CH_3CH_2$ | $CH_2CONHCH_2CH_3$ | H | H | $CH_2CH_2$ | 551 (MH) |
| 141 | H | H | $CH_3$ | $CH_3CH_2$ | $CH_2CH_2C(O)NH$-(4-pyridyl N-oxide) | H | H | $CH_2CH_2$ | 616 (MH) |
| 142 | H | H | $CH_3$ | $CH_3CH_2$ | $CH_2CH_2$-O-(4-pyridyl) | H | H | $CH_2CH_2$ | 587 (MH) |
| 143 | H | H | $CH_3$ | $CH_3CH_2$ | $CH_2CH_2$-O-(4-pyridyl N-oxide) | H | H | $CH_2CH_2$ | 603 (MH) |
| 144 | H | $CH_3$ | H | cyclopropyl | 4-pyridyl N-oxide-methyl | H | H | $CH_2CH_2$ | 585 (MH) |
| 145 | F | $CH_3$ | H | $CH_3CH_2$ | 4-pyridyl N-oxide-methyl | H | H | $CH_2CH_2$ | 591 (MH) |
| 146 | Cl | $CH_3$ | H | $CH_3CH_2$ | 4-pyridyl N-oxide-methyl | H | H | $CH_2CH_2$ | 607 (MH), 609 (MH) |
| 147 | Cl | $CH_3$ | H | $CH_3CH_2$ | $CH_2CH_2C(O)NH$-(4-pyridyl N-oxide) | H | H | $CH_2CH_2$ | 650 (MH), 652 (MH) |

TABLE 1-continued

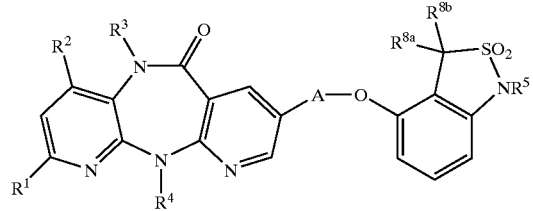

| Cmpd No. | R¹ | R² | R³ | R⁴ | R⁵ | R⁸ᵃ | R⁸ᵇ | A | m/z (ES+) |
|---|---|---|---|---|---|---|---|---|---|
| 148 | F | H | CH₃ | CH₃CH₂ | 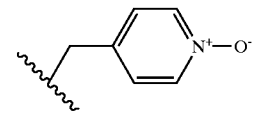 | H | H | CH₂ | 577 (MH) |

TABLE 2

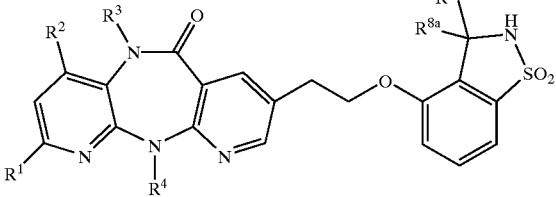

| Cmpd No. | R¹ | R² | R³ | R⁴ | R⁸ᵃ | R⁸ᵇ | m/z (ES+) |
|---|---|---|---|---|---|---|---|
| 202 | H | H | CH₃ | CH₃CH₂ | H | H | 466 (MH) 488 (M + 23) |
| 223 | F | CH₃ | H | CH₃CH₂ | H | H | 484 (MH) |
| 224 | H | H | CH₃ | CH₃CH₂ | CH₃ | CH₃ | 494 (MH) |
| 226 | H | CH₃ | H | cyclopropyl | CH₃ | CH₃ | 506 (MH) |

TABLE 3

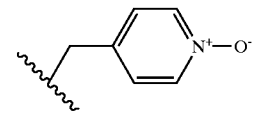

| Cmpd No. | R¹ | R² | R³ | R⁵ | R⁸ᴬ | R⁸ᴮ | m/z (ES+) |
|---|---|---|---|---|---|---|---|
| 301 | H | H | CH₃ | H | H | H | 466 (MH), 488 (M + 23) |
| 303 | H | H | CH₃ | CH₃ | H | H | 480 (MH) |
| 306 | H | H | CH₃ | H | CH₃ | CH₃ | 494 (MH), 516 (M + 23) |
| 307 | H | H | CH₃ | CH₃ | CH₃ | CH₃ | 508 (MH), 530 (M + 23) |
| 310 | F | CH₃ | H | H | H | H | 484 (MH) |
| 311 | H | CH₃ | H | H | CH₃ | CH₃ | 494 (MH) |
| 325 | F | CH₃ | H | H | CH₃ | CH₃ | 498 (MH) |

TABLE 4

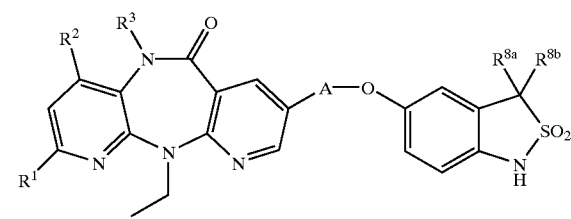

| Cmpd No. | R¹ | R² | R³ | R⁸ᴬ | R⁸ᴮ | A | m/z (ES+) |
|---|---|---|---|---|---|---|---|
| 402 | H | H | CH₃ | H | H | CH₂CH₂ | 466 (MH) |
| 404 | F | H | CH₃ | H | H | CH₂ | 470 (MH) |
| 409 | F | CH₃ | H | CH₃ | CH₃ | CH₂CH₂ | 512 (MH) |

TABLE 5

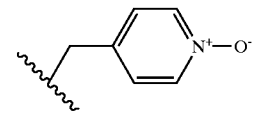

| Cmpd No. | R⁵ | m/z (ES+) |
|---|---|---|
| 505 | H | 480 (MH) |
| 508 | CH₃ | 494 (MH) |

TABLE 6

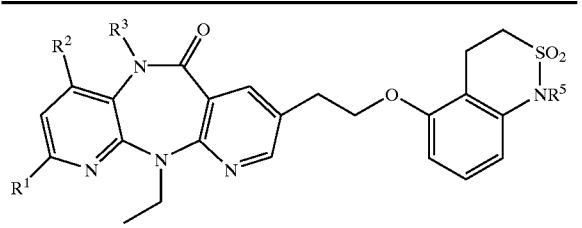

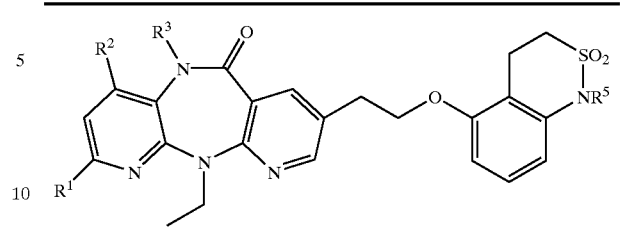

| Cmpd No. | R¹ | R² | R³ | R⁵ | m/z (ES+) |
|---|---|---|---|---|---|
| 601 | H | H | CH₃ | H | 480 (MH), 502 (M + 23) |
| 602 | F | CH₃ | H | H | 498 (MH) |
| 617 | H | H | CH₃ | -CH₂CH₂-morpholine | 593 (MH) |
| 609 | H | H | CH₃ | CH₂CONH₂ | 537 (MH) |
| 618 | H | H | CH₃ | -C(O)-morpholine | 593 (MH) |
| 619 | H | H | CH₃ | -C(O)-pyrrolidine | 577 (MH) |
| 610 | H | H | CH₃ | CON(CH₂CH₃)₂ | 579 (MH) |
| 620 | H | H | CH₃ | -C(O)-N-methylpiperazine | 606 (MH) |
| 611 | H | H | CH₃ | CON(CH₃)OCH₃ | 567 (MH) |
| 613 | H | H | CH₃ | CH₂CH₂N(CH₂CH₃)₂ | 579 (MH) |
| 621 | H | H | CH₃ | -CH₂-4-pyridyl | 571 (MH) |
| 614 | H | H | CH₃ | CH₂CO₂H | 538 (MH) |
| 622 | H | H | CH₃ | -CH₂-(2-methylthiazol-4-yl) | 591 (MH) |
| 623 | H | H | CH₃ | -CH₂CH₂C(O)-pyrrolidine | 591 (MH) |
| 615 | H | H | CH₃ | CH₂CH₂OH | 524 (MH) |
| 616 | H | H | CH₃ | CH₂CO₂Me | 550 (M − H) |
| 624 | H | H | CH₃ | -CH₂-(4-pyridyl N-oxide) | 587 (MH) |
| 625 | H | H | CH₃ | CH₂CH₂CH₂CO₂H | 566 (MH) |
| 626 | H | H | CH₃ | -CH₂-tetrazole | 562 (MH) |
| 627 | H | H | CH₃ | CH₂SO₂CH₃ | 572 (MH) |
| 628 | H | H | CH₃ | (CH₂)₃COOCH₂CH₃ | 594 (MH) |
| 629 | H | H | CH₃ | -CH₂-3-pyridyl | 571 (MH) |
| 630 | H | H | CH₃ | (CH₂)₃SO₂NH₂ | 601 (MH) |
| 631 | H | H | CH₃ | CH₂CONHSO₂CH₃ | 615 (MH) |
| 632 | H | H | CH₃ | -CH₂-(3-pyridyl N-oxide) | 587 (MH) |
| 633 | H | H | CH₃ | (CH₂)₂SO₃H | 602 (MH) |
| 634 | H | H | CH₃ | (CH₂)₂C(CH₂)₂COOH | 594 (MH) |
| 635 | H | H | CH₃ | (CH₂)₃CONH₂ | 565 (MH) |
| 636 | H | H | CH₃ | (CH₂)₃CONHNH₂ | 580 (MH) |
| 637 | H | H | CH₃ | -CH₂C(O)NH-C(CH₃)₂-COOH | 623 (MH) |
| 638 | H | H | CH₃ | -CH₂C(O)NH-cyclopropyl-COOH | 621 (MH) |
| 639 | H | H | CH₃ | CH₂CH₂OCONH₂ | 567 (MH) |
| 640 | H | H | CH₃ | (CH₂)₃CONHNHCH₂CF₃ | 662 (MH) |
| 641 | H | H | CH₃ | CH₂CONHC(CH₃)₂CONHNH₂ | 637 (MH) |
| 642 | H | H | CH₃ | -CH₂CH₂-(imidazol-2-yl) | 560 (MH) |

TABLE 7

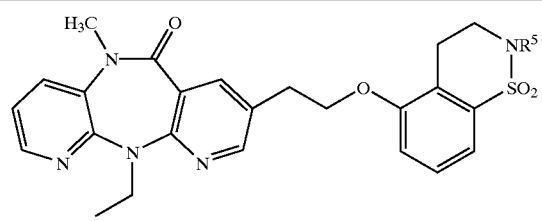

| Cmpd No. | R⁵ | m/z (ES+) |
|---|---|---|
| 712 | H | 480 (MH) |
| 713 | (CH₂)₃COOH | 566 (MH) |
| 714 | (CH₂)₃CONHNH₂ | 580 (MH) |

TABLE 8

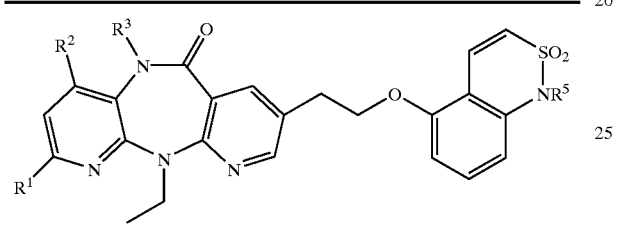

| Cmpd No. | R¹ | R² | R³ | R⁵ | m/z (ES+) |
|---|---|---|---|---|---|
| 803 | H | H | CH₃ | CH₃ | 492 (MH) |
| 804 | H | CH₃ | H | CH₃ | 492 (MH), 514 (M + 23) |
| 805 | H | H | H | CH₃ | 478 (MH) |
| 806 | H | H | CH₃CH₂ | CH₃ | 506 (MH) |
| 807 | H | H | CH₃ | CH₂CH₃ | 506 (MH) |
| 808 | H | H | CH₃ | H | 478 (MH) |
| 809 | H | H | CH₃ | (CH₂)₃COOH | 564 (MH) |

TABLE 9

| Cmpd no. | $IC_{50}$ WT RT | $IC_{50}$ K103N/ Y181C | $EC_{50}$ WT RT | $EC_{50}$ K103N/ Y181C |
|---|---|---|---|---|
| 101 | C | B | — | C |
| 202 | C | C | C | C |
| 103 | C | B | C | C |
| 104 | A | — | — | — |
| 105 | C | — | — | — |
| 106 | C | — | — | — |
| 107 | C | — | — | — |
| 108 | B | — | — | — |
| 109 | C | B | — | — |
| 110 | C | B | C | C |
| 111 | C | C | — | — |
| 112 | C | C | — | — |
| 113 | C | B | — | — |
| 114 | C | C | — | — |
| 115 | C | C | — | — |
| 116 | C | B | — | — |
| 117 | C | C | C | — |
| 118 | C | B | — | — |
| 119 | C | B | — | — |
| 120 | B | — | — | — |
| 121 | C | B | — | — |
| 122 | C | C | — | — |
| 223 | C | C | C | C |
| 127 | C | B | C | B |
| 128 | C | C | C | C |
| 129 | C | C | C | C |
| 130 | C | C | C | C |

TABLE 9-continued

| Cmpd no. | $IC_{50}$ WT RT | $IC_{50}$ K103N/ Y181C | $EC_{50}$ WT RT | $EC_{50}$ K103N/ Y181C |
|---|---|---|---|---|
| 148 | C | — | — | — |
| 301 | C | B | — | — |
| 402 | C | A | — | — |
| 303 | C | B | — | — |
| 404 | C | A | — | — |
| 306 | C | C | — | — |
| 307 | C | B | — | — |
| 409 | C | B | — | — |
| 310 | C | B | — | — |
| 311 | C | B | C | C |
| 601 | C | C | C | C |
| 602 | C | C | C | C |
| 803 | C | C | C | C |
| 804 | C | C | C | C |
| 224 | C | B | — | — |
| 805 | C | B | — | — |
| 807 | C | C | — | — |
| 806 | C | C | — | — |
| 325 | C | A | — | — |
| 808 | B | — | — | — |
| 617 | C | C | C | C |
| 226 | C | A | — | — |
| 609 | C | C | — | — |
| 618 | C | C | — | — |
| 619 | C | C | — | — |
| 610 | C | C | — | — |
| 620 | C | C | — | — |
| 611 | C | C | — | — |
| 712 | C | C | — | — |
| 613 | C | C | — | — |
| 616 | C | C | C | C |
| 621 | C | C | C | C |
| 614 | C | C | — | — |
| 622 | C | C | — | — |
| 623 | C | C | — | — |
| 625 | C | C | C | C |
| 131 | C | C | C | C |
| 132 | C | C | C | C |
| 133 | C | C | — | — |
| 134 | C | C | — | — |
| 135 | C | C | — | — |
| 136 | C | C | C | C |
| 137 | C | C | C | C |
| 138 | C | C | C | C |
| 139 | C | B | — | — |
| 140 | C | C | — | — |
| 141 | C | C | C | C |
| 142 | C | C | — | — |
| 143 | C | C | — | — |
| 144 | C | B | — | — |
| 145 | C | C | — | — |
| 146 | C | C | — | — |
| 147 | C | C | C | C |
| 627 | C | C | — | — |
| 628 | C | C | C | C |
| 629 | C | C | C | C |
| 630 | C | C | C | C |
| 631 | C | C | B | B |
| 632 | C | C | — | — |
| 633 | C | C | B | A |
| 634 | C | C | C | C |
| 635 | C | C | — | — |
| 636 | C | C | C | C |
| 637 | C | C | C | C |
| 638 | C | C | C | C |
| 639 | C | C | C | C |
| 640 | C | C | C | C |
| 641 | C | C | C | C |
| 642 | C | C | — | — |
| 713 | C | C | C | C |
| 714 | C | C | C | C |
| 809 | C | B | C | C |

In Table 9 above, the following ranges apply: A=>1 µM; B=<1 µM>100 nM; C=<100 nM. The hyphen in Table 9 denotes not determined.

We claim:

1. A compound of formula I:

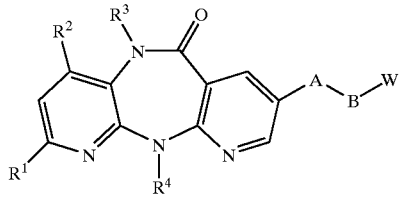

wherein

A is a connecting chain of $(C_{1-3})$ alkyl;

B is O or S;

$R^1$ is H, $(C_{1-6})$ alkyl, halo, $CF_3$, or $OR^{1a}$ wherein $R^{1a}$ is H or $(C_{1-6})$alkyl;

$R^2$ is H or Me;

$R^3$ is H or Me;

$R^4$ is selected from the group consisting of: H, $(C_{1-4})$alkyl, $(C_{3-4})$ cycloalkyl and $(C_{1-4})$alkyl-$(C_{3-7})$cycloalkyl;

W is selected from

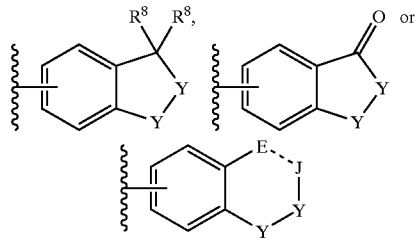

wherein, a) one of Y is $SO_2$ and the other Y is $NR^5$, provided that both are not the same, wherein $R^5$ is selected from the group consisting of: H, $(C_{1-6})$alkyl, $(C_{3-6})$ cycloalkyl, said alkyl being optionally substituted with a substituent selected from the group consisting of:
(i) $(C_{3-6}$ cycloalkyl);
(ii) 5- or 6-membered heterocycle having 1 to 4 heteroatoms selected from O, N, and S, said heterocycle being optionally substituted with $(C_{1-6})$alkyl;
(iii) $NR^{5a}R^{5b}$, wherein each of $R^{5a}$ and $R^{5b}$ is H or $(C_{1-6})$alkyl said alkyl being optionally substituted with $(C_{1-6})$alkoxy, $(C_{6-10})$aryl or 5- or 6-membered heterocycle having 1 to 4 heteroatom selected from O, N, and S, said heterocycle being optionally mono- or di-substituted with $(C_{1-6})$ alkyl;
(iv) $OR^{5c}$ wherein $R^{5c}$ is H, $(C_{1-6})$ alkyl or 5- or 6-membered heterocycle having 1 to 4 heteroatoms selected from O, N, and S;
(v) $OCONR^{5d}R^{5e}$, wherein $R^{5d}$ and $R^{5e}$ are both H; or $R^{5d}$ is H and $R^{5e}$ is $(C_{1-6})$alkyl;
(vi) $COOR^{5f}$, wherein $R^{5f}$ is H or $(C_{1-6})$alkyl;
(vii) $CONR^{5g}R^{5h}$ wherein each of $R^{5g}$ and $R^{5h}$ is H or $(C_{1-6})$alkyl; or $R^{5g}$ is H and $R^{5h}$ is $(C_{3-7})$ cycloalkyl, said alkyl and said cycloalkyl being optionally substituted with $COOR^{5i}$ wherein $R^{5i}$ is selected from the group consisting of:

H and $(C_{1-6})$alkyl; or $CONHNH_2$; or OH or $(C_{1-6})$alkoxy; or $(C_{6-10})$aryl; or 5- or 6-membered heterocycle having 1 to 4 heteroatom selected from O, N, and S, said heterocycle being optionally mono- or di-substituted with $(C_{1-6})$alkyl;

or $R^{5h}$ is $NR^{5j}R^{5k}$ wherein when $R^{5j}$ and $R^{5k}$ are both H;

or $R^{5j}$ is H and $R^{5k}$ is $CH_2CF_3$;

or $R^{5h}$ is 5- or 6-membered heterocycle having 1 to 4 heteroatoms selected from O, N, and S;

(viii) $COR^{5l}$ wherein $R^{5l}$ is $(C_{1-6})$ alkyl or 5- or 6-membered heterocycle having 1 to 4 heteroatoms selected from O, N, and S, said heterocycle being optionally substituted with $(C_{1-6})$alkyl;

(ix) $SO_2R^{5m}$, wherein $R^{5m}$ is $(C_{1-6})$alkyl or $NH_2$; and (x) $SO_3H$, or $R^5$ is $COR^{5n}$ wherein $R^{5n}$ is $(C_{1-6})$ alkyl or 5- or 6-membered heterocycle having 1 to 4 heteroatoms selected from O, N, and S, said heterocycle being optionally substituted with $(C_{1-6})$alkyl;

$COOR^{5o}$ wherein $R^{5o}$ is $(C_{1-6})$ alkyl;

$CONR^{5p}R^{5q}$ wherein each of $R^{5p}$ and $R^{5q}$ is H, OH, $(C_{1-6})$alkoxy, or $(C_{1-6})$alkyl said alkyl being optionally substituted with $(C_{1-6})$alkoxy, $(C_{6-10})$aryl, 5- or 6-membered heterocycle having 1 to 4 heteroatom selected from O, N, and S, said heterocycle being optionally mono- or di-substituted with $(C_{1-6})$alkyl; and $COCH_2NR^{5r}R^{5s}$ wherein each of $R^{5r}$ and $R^{5s}$ is H or $(C1-6)$alkyl, said alkyl being optionally substituted with $(C_{1-6})$alkoxy, $(C_{6-10})$aryl, or 5- or 6-membered heterocycle having 1 to 4 heteroatom selected from O, N, and S, said heterocycle being optionally mono- or di-substituted with $(C_{1-6})$alkyl;

and each $R^8$ is independently H, $(C_{1-4})$ alkyl, $(C_{3-6})$ cycloalkyl, or $(C_{1-4})$ alkyl-$(C_{3-6})$ cycloalkyl; or b) E is $CR^{8a}R^{8b}$ wherein each of $R^{8a}$ and $R^{8b}$ is H, $(C_{1-4})$ alkyl, $(C_{3-6})$ cycloalkyl, or $(C_{1-4})$ alkyl-$(C_{3-6})$ cycloalkyl, and J is $CH_2$; or J is $CR^{8a}R^{8b}$ wherein $R^{8a}$ and $R^{8b}$ are as defined above and E is $CH_2$, wherein the dotted line represents a single bond; or c) E is $C(O)$ and J is $OR^{8a}R^{8b}$ wherein $R^{8a}$ and $R^{8b}$ are as defined above; or J is $C(O)$ and E is $CR^{8a}R^{8b}$ wherein $R^{8a}$ and $R^{8b}$ are as defined above, wherein the dotted line represents a single bond; or d) both E and J are $CR^8$ wherein $R^8$ is as defined above, wherein the dotted line represents a double bond;

or a salt or a prodrug thereof.

2. A compound according to claim 1, in which $R^5$ is selected from the group consisting of: H, $(C_{1-6})$alkyl and $(C_{3-6})$ cycloalkyl, said alkyl being optionally substituted with a substituent selected from the group consisting of:
(i) $(C_{3-6}$ cycloalkyl);
(iii) $NR^{5a}R^{5b}$, wherein each of $R^{5a}$ and $R^{5b}$ is H or $(C1-6)$alkyl, said alkyl being optionally substituted with $(C_{1-6})$alkoxy, $(C_{6-10})$aryl, or 5- or 6-membered heterocycle having 1 to 4 heteroatom selected from O, N, and S, said heterocycle being optionally mono- or di-substituted with $(C_{1-6})$alkyl;
(iv) $OR^{5c}$ wherein $R^{5c}$ is H, $(C_{1-6})$ alkyl;
(vi) $COOR^{5f}$, wherein $R^{5f}$ is H or $(C1-6)$alkyl;
(vii) $CONR^{5g}R^{5h}$ wherein each of $R^{5g}$ and $R^{5h}$ is H or $(C_{1-6})$alkyl; or $R^{5g}$ is H and $R^{5h}$ is $(C_{1-6})$alkyl said alkyl being optionally substituted with $(C_{1-6})$alkoxy, $(C_{6-10})$aryl, or 5- or 6-membered heterocycle having 1 to 4 heteroatom selected from O, N, and S, said heterocycle being optionally mono- or di-substituted with $(C_{1-6})$alkyl;

or $R^5$ is $COR^{5n}$ wherein $R^{5n}$ is $(C_{1-6})$ alkyl;

$COOR^{5o}$ wherein $R^{5o}$ is $(C_{1-6})$ alkyl;

$CONR^{5p}R^{5q}$ wherein each of $R^{5p}$ and $R^{5q}$ is H, OH, $(C_{1-6})$alkoxy, $(C_{1-6})$alkyl, said alkyl being optionally substituted with $(C_{1-6})$alkoxy, $(C_{6-10})$aryl, or 5- or 6-membered heterocycle having 1 to 4 heteroatom selected from O, N, and S, said heterocycle being optionally mono- or di-substituted with $(C_{1-6})$alkyl; and $COCH_2NR^{5r}R^{5s}$ wherein each of $R^{5r}$ and $R^{5s}$ is H or $(C_{1-6})$alkyl said alkyl being optionally substituted with $(C_{1-6})$alkoxy, $(C_{6-10})$aryl, or 5- or 6-membered heterocycle having 1 to 4 heteroatom selected from O, N, and S, said heterocycle being optionally mono- or di-substituted with $(C_{1-6})$alkyl.

3. A compound according to claim 1, having the following formula:

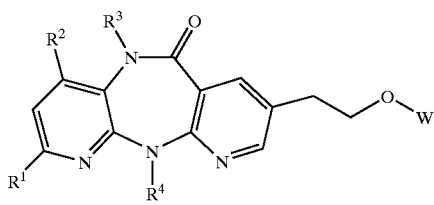

Ia wherein $R^1$, $R^2$, $R^3$, $R^4$, and W are as defined in claim 1.

4. A compound according to claim 3, wherein $R^1$ is H, Me, or F.

5. A compound according to claim 4, wherein $R^1$ is H or F.

6. A compound according to claim 3, wherein $R^2$ is H.

7. A compound according to claim 3, wherein $R^3$ is $CH_3$.

8. A compound according to claim 3, wherein $R^4$ is Et or cyclopropyl.

9. A compound according to claim 8, wherein $R^4$ is Et.

10. A compound according to claim 1, wherein W is

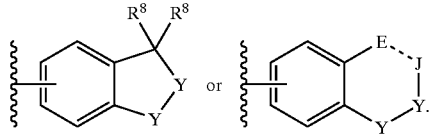

wherein E, J, Y and $R^8$ are as defined in claim 1.

11. A compound according to claim 1, wherein $R^5$ is selected from the group consisting of: H, $(C_{1-6})$alkyl, said alkyl being optionally substituted with a substituent selected from the group consisting of:
  (i) $(C_{3-6}$ cycloalkyl);
  (ii) 5- or 6-membered heterocycle having 1 to 4 heteroatom selected from O, N, and S, said heterocycle being optionally substituted with $(C_{1-6})$ alkyl;
  (iii) $NR^{5a}R^{5b}$, wherein each of $R^{5a}$ and $R^{5b}$ is H; or $(C_{1-6})$alkyl;
  (iv) $OR^{5c}$ wherein $R^{5c}$ is H, $(C_{1-6})$ alkyl or 5- or 6-membered heterocycle having 1 to 4 heteroatom selected from O, N, and S;
  (v) $OCONR^{5d}R^{5e}$, wherein $R^{5d}$ and $R^{5e}$ are both H; or $R^{5d}$ is H and $R^{5e}$ is $(C_{1-6})$alkyl;
  (vi) $COOR^{5f}$, wherein $R^{5f}$ is H or $(C_{1-6})$alkyl;
  (vii) $CONR^{5g}R^{5h}$ wherein each of $R^{5g}$ and $R^{5h}$ is H or $(C_{1-6})$alkyl; or $R^{5g}$ is H and $R^{5h}$ is $(C_{3-7})$cycloalkyl, said alkyl and said cycloalkyl being optionally substituted with $COOR^{5i}$ wherein $R^{5i}$ is selected from the group consisting of:
    H and $(C_{1-6})$alkyl; or $CONHNH_2$;
    or $R^{5h}$ is $NH_2$ or $NHCH_2CF_3$;
    or $R^{5h}$ is 5- or 6-membered heterocycle having 1 to 4 heteroatom selected from O, N, and S;
  (viii) $COR^{5l}$ wherein $R^{5l}$ is $(C_{1-6})$ alkyl or 5- or 6-membered heterocycle having 1 to 4 heteroatom selected from O, N, and S, said heterocycle being optionally substituted with $(C_{1-6})$alkyl;
  (ix) $SO_2R^{5m}$, wherein $R^{5m}$ is $(C_{1-6})$alkyl or $NH_2$; and
  (x) $SO_3H$,
or $R^5$ is $COR^{5n}$ wherein $R^{5n}$ is $(C_{1-6})$ alkyl or 5- or 6-membered heterocycle having 1 to 4 heteroatom selected from O, N, and S, said heterocycle being optionally substituted with $(C_{1-6})$ alkyl;

$COOR^{5o}$ wherein $R^{5o}$ is $(C_{1-6})$ alkyl; and $CONR^{5p}R^{5q}$ wherein each of $R^{5p}$ and $R^{5q}$ is H, $(C_{1-6})$ alkyl, OH or $(C_{1-6})$alkoxy.

12. A compound according to claim 11, wherein $R^5$ is H or $(C_{1-6})$alkyl said alkyl being optionally substituted with a substituent selected from the group consisting of:
  (i) $(C_{3-6}$ cycloalkyl);
  (ii) 5- or 6-membered heterocycle having 1 to 4 heteroatom selected from O, N, and S, said heterocycle being optionally substituted with $(C_{1-6})$ alkyl;
  (iii) $NR^{5a}R^{5b}$, wherein each of $R^{5a}$ and $R^{5b}$ is H or $(C_{1-6})$alkyl;
  (iv) OH;
  (vi) $COOR^{5f}$, wherein $R^{5f}$ is H or $(C_{1-6})$alkyl;
  (vii) $CONR^{5g}R^{5h}$ wherein $R^{5g}$ and $R^{5h}$ are both H; or $R^{5g}$ is H and $R^{5h}$ is $NH_2$; and
  (viii) $COR^{5l}$ wherein $R^{5l}$ is $(C_{1-6})$ alkyl or 5- or 6-membered heterocycle having 1 to 4 heteroatom selected from O, N, and S, said heterocycle being optionally substituted with $(C_{1-6})$alkyl;

or $R^5$ is $COR^{5n}$ wherein $R^{5n}$ is $(C_{1-6})$ alkyl or 5- or 6-membered heterocycle having 1 to 4 heteroatom selected from O, N, and S, said heterocycle being optionally substituted with $(C_{1-6})$alkyl;

$COOR^{5o}$ wherein $R^{5o}$ is $(C_{1-6})$ alkyl; and $CONR^{5p}R^{5q}$ wherein each of $R^{5p}$ and $R^{5q}$ is $(C_{1-6})$alkyl, or $(C_{1-6})$alkoxy.

13. A compound according to claim 12, wherein $R^5$ is selected from the group consisting of: H and $(C_{1-6})$alkyl said alkyl being optionally substituted with COOH.

14. A compound according to claim 1, wherein each $R^8$ is independently H, or $(C_{1-4})$ alkyl.

15. A compound according to claim 14, wherein each of $R^8$ is H or $CH_3$.

16. A compound according to claim 15, wherein each of $R^8$ is H.

17. A compound according to claim 10, wherein W is:

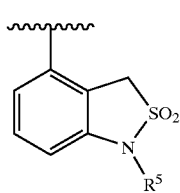

I(b)

wherein $R^5$ is selected from the group consisting of: H, $(C_{1-6})$alkyl, said alkyl being optionally substituted with a substituent selected from the group consisting of:
(i) $(C_{3-6})$cycloalkyl;
(ii) 5- or 6-membered heterocycle having 1 to 4 heteroatom selected from O, N, and S, said heterocycle being optionally substituted with $(C_{1-6})$alkyl; and
(vi) $COOR^{5f}$, wherein $R^{5f}$ is H or $(C_{1-6})$alkyl;
or $R^5$ is $COOR^{5o}$ wherein $R^{5o}$ is $(C_{1-6})$ alkyl.

18. A compound according to claim 17, wherein $R^{5f}$ is H.

19. A compound according to claim 17, wherein $R^{5o}$ is $(C_{1-6})$alkyl.

20. A compound according to claim 19, wherein $R^{5o}$ is ethyl.

21. A compound according to claim 17, wherein $R^5$ is selected from the group consisting of: H, $CH_3$, $CH_3CH_2$,

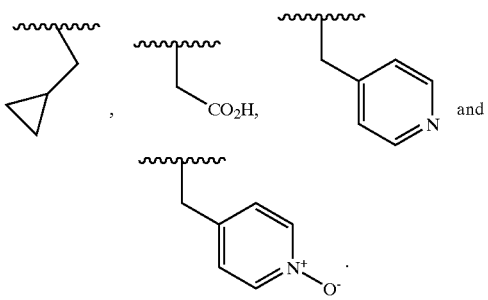

22. A compound according to claim 21, wherein $R^5$ is selected from the group consisting of: H, $CH_3$, $CH_3CH_2$,

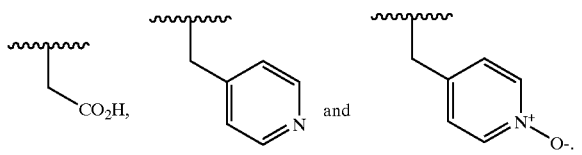

23. A compound according to claim 10, wherein W is:

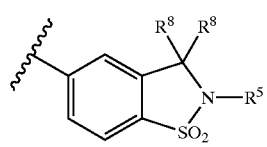

I(c)

wherein $R^5$ is H or $(C_{1-6})$alkyl, and each of $R^8$ is H or $CH_3$.

24. A compound according to claim 23, wherein $R^5$ is H or $CH_3$.

25. A compound according to claim 10, wherein W is

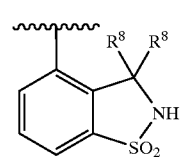

I(d)

wherein each of $R^8$ is H or $CH_3$.

26. A compound according to claim 1, wherein W is:

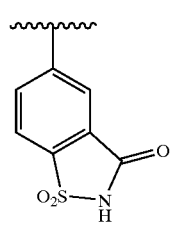

I(f)

27. A compound according to claim 1, wherein W is:

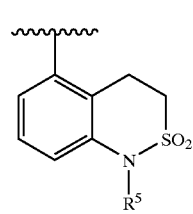

I(g)

wherein $R^5$ is selected from the group consisting of: H, $(C_{1-6})$alkyl, said alkyl being optionally substituted with a substituent selected from the group consisting of:
(ii) 5- or 6-membered heterocycle having 1 to 4 heteroatoms selected from O, N, and S, said heterocycle being optionally substituted with $(C_{1-6})$alkyl;
(iii) $NR^{5a}R^{5b}$, wherein each of $R^{5a}$ and $R^{5b}$ is H or $(C_{1-6})$alkyl;
(iv) OH or $(C_{1-6})$alkoxy;
(vi) $COOR^{5f}$, wherein $R^{5f}$ is H or $(C_{1-6})$alkyl; or
(vii) $CONH_2$; and
(viii) $COR^{5l}$ wherein $R^{5l}$ is $(C_{1-6})$ alkyl or 5- or 6-membered heterocycle having 1 to 4 heteroatoms selected from O, N, and S, said heterocycle being optionally substituted with $(C_{1-6})$alkyl;
or $R^5$ is $COR^{5n}$ wherein $R^{5n}$ is $(C_{1-6})$ alkyl or 5- or 6-membered heterocycle having 1 to 4 heteroatoms selected from O, N, and S, said heterocycle being optionally substituted with $(C_{1-6})$alkyl; and
$CONR^{5p}R^{5q}$ wherein each of $R^{5p}$ and $R^{5q}$ is H, $(C_{1-6})$ alkyl, OH or $(C_{1-6})$alkoxy.

28. A compound according to claim 27, wherein $R^5$ is selected from the group consisting of:

29. A compound according to claim 27, wherein $R^5$ is selected from the group consisting of:

[chemical structures]

30. A compound according to claim 27, wherein $R^{5a}$ and $R^{5b}$ are both $(C_{1-6})$ alkyl.
31. A compound according to claim 30, wherein $R^{5a}$ and $R^{5b}$ are both ethyl.
32. A compound according to claim 27, wherein $R^5$ is OH.
33. A compound according to claim 27, wherein $R^{5f}$ is H or methyl.
34. A compound according to claim 27, wherein $R^{5l}$ is

[chemical structure]

35. A compound according to claim 27, wherein $R^{5p}$ and $R^{5q}$ are both $(C_{16})$alkyl.
36. A compound according to claim 35, wherein $R^{5p}$ and $5^{5q}$ are both ethyl.
37. A compound according to claim 27, wherein when $R^{5p}$ is $(C_{1-6})$alkyl, then $R^{5q}$ is OH or $(C_{1-6})$alkoxy.
38. A compound according to claim 37, wherein $R^{5p}$ is methyl and $R^{5q}$ is $(C_{1-6})$alkoxy.
39. A compound according to claim 38, wherein $R^{5q}$ is $OCH_3$.
40. A compound according to claim 1, wherein W is:

I(h)

[chemical structure]

wherein $R^5$ is H, $(C_{1-6})$alkyl wherein said alkyl is substituted with a substituent selected from the group consisting of:

(iii) $COOR^{5f}$, wherein $R^{5f}$ is H or $(C_{1-6})$alkyl; and
(vii) $CONHNH_2$.

41. A compound according to claim 40 in which $R^5$ is $(CH_2)_3COOH$ and $(CH_2)_3CONHNH_2$.
42. A compound according to claim 1, wherein W is I(i)

[chemical structure]

wherein $R^5$ is selected from the group consisting of: H, $(C_{1-6})$alkyl and $(CH_2)_3COOH$.

43. A compound according to claim 42, wherein $R^5$ is H or $CH_3$.
44. A compound according to claim 1 having the following formula:

[chemical structure]

wherein $R^1$, $R^2$, $R^3$, $R^4$ and $R^5$ are as defined in claim 1.

45. A compound according to claim 1, having the following formula:

[chemical structure]

wherein $R^1$, $R^2$, $R^3$, $R^4$ and $R^5$ are as defined in claim 1.

46. A compound according to claim 1, having the following formula:

[chemical structure]

wherein $R^1$, $R^2$, $R^3$, $R^4$, $R^5$ and $R^8$ are as defined in claim 1.

47. A compound according to claim 1, having the following formula:

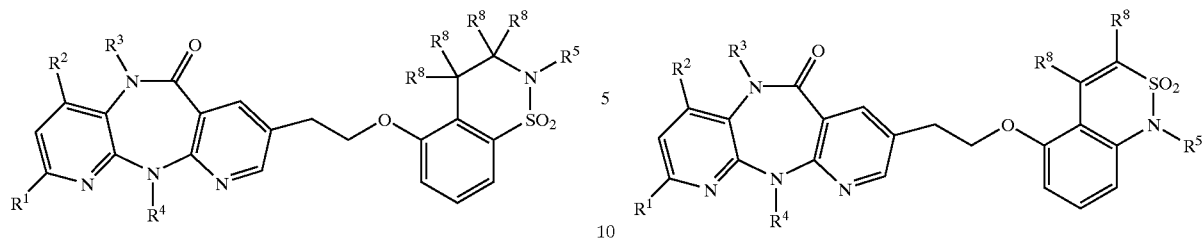

wherein $R^1$, $R^2$, $R^3$, $R^4$, $R^5$ and $R^8$ are as defined in claim 1.

48. A compound according to claim 1, having the following formula:

wherein $R^1$, $R^2$, $R^3$, $R^4$, $R^5$ and $R^8$ are as defined in claim 1.

49. The compound according to claim 1, having the following formula

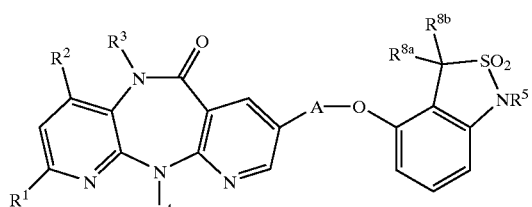

wherein $R^1$, $R^2$, $R^3$, $R^4$ $R^5$, $R^{8a}$, $R^{8b}$, and A are defined as follows:

| Cmpd No. | $R^1$ | $R^2$ | $R^3$ | $R^4$ | $R^5$ | $R^{8a}$ | $R^{8b}$ | A |
|---|---|---|---|---|---|---|---|---|
| 101 | H | H | $CH_3$ | $CH_3CH_2$ | H | H | H | $CH_2CH_2$ ; |
| 103 | F | H | $CH_3$ | $CH_3CH_2$ | H | H | H | $CH_2CH_2$ ; |
| 104 | F | H | $CH_3$ | $CH_3CH_2$ | H | H | H | $CH_2$ ; |
| 105 | H | H | $CH_3$ | cyclopropyl | H | H | H | $CH_2CH_2$ ; |
| 106 | F | $CH_3$ | H | cyclopropyl | H | H | H | $CH_2CH_2$ ; |
| 107 | F | H | $CH_3$ | $CH_3CH_2$ | $CH_3$ | H | H | $CH_2$ ; |
| 108 | F | H | $CH_3$ | $CH_3CH_2$ | $CH_3$ | H | $CH_3$ | $CH_2$ ; |
| 109 | $CH_3$ | $CH_3$ | H | $CH_3CH_2$ | H | H | H | $CH_2CH_2$ ; |
| 110 | F | $CH_3$ | H | $CH_3CH_2$ | H | H | H | $CH_2CH_2$ ; |
| 111 | F | H | $CH_3$ | $CH_3CH_2$ | $CH_3$ | H | H | $CH_2CH_2$ ; |
| 112 | F | $CH_3$ | H | $CH_3CH_2$ | $CH_3$ | H | H | $CH_2CH_2$ ; |
| 113 | $CH_3$ | H | $CH_3$ | $CH_3CH_2$ | H | H | H | $CH_2CH_2$ ; |
| 114 | $CH_3$ | H | $CH_3$ | $CH_3CH_2$ | $CH_3$ | H | H | $CH_2CH_2$ ; |
| 115 | $CH_3$ | H | $CH_3$ | $CH_3CH_2$ | $CH_2CH_3$ | H | H | $CH_2CH_2$ ; |
| 116 | H | H | $CH_3$ | cyclopropyl | $CH_3$ | H | H | $CH_2CH_2$ ; |
| 117 | $CH_3$ | $CH_3$ | H | $CH_3CH_2$ | $CH_3$ | H | H | $CH_2CH_2$ ; |
| 118 | F | $CH_3$ | H | cyclopropyl | $CH_3$ | H | H | $CH_2CH_2$ ; |
| 119 | F | $CH_3$ | $CH_3$ | cyclopropyl | $CH_3$ | H | H | $CH_2CH_2$ ; |
| 120 | H | $CH_3$ | H | $CH_3CH_2$ | H | H | H | $CH_2CH_2$ ; |
| 121 | H | $CH_3$ | H | $CH_3CH_2$ | ⸺CH₂-cyclopropyl | H | H | $CH_2CH_2$ ; |
| 122 | H | H | $CH_3$ | $CH_3CH_2$ | $CO_2CH_2CH_3$ | H | H | $CH_2CH_2$ ; |
| 127 | H | H | $CH_3$ | $CH_3CH_2$ | $CH_2COOH$ | H | H | $CH_2CH_2$ ; |
| 128 | H | H | $CH_3$ | $CH_3CH_2$ | ⸺CH₂-(4-pyridyl) | H | H | $CH_2CH_2$ ; |
| 129 | H | H | $CH_3$ | $CH_3CH_2$ | $CH_2CH_2OH$ | H | H | $CH_2CH_2$ ; |
| 130 | H | H | $CH_3$ | $CH_3CH_2$ | ⸺CH₂-(4-pyridyl N-oxide) | H | H | $CH_2CH_2$ ; |

-continued

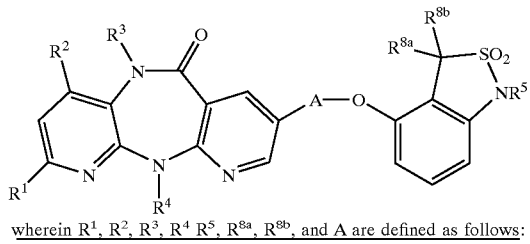

wherein $R^1$, $R^2$, $R^3$, $R^4$ $R^5$, $R^{8a}$, $R^{8b}$, and A are defined as follows:

| Cmpd No. | $R^1$ | $R^2$ | $R^3$ | $R^4$ | $R^5$ | $R^{8a}$ | $R^{8b}$ | A | |
|---|---|---|---|---|---|---|---|---|---|
| 131 | H | H | $CH_3$ | $CH_3CH_2$ | 3-pyridylmethyl | H | H | $CH_2CH_2$ | ; |
| 132 | H | H | $CH_3$ | $CH_3CH_2$ | (3-pyridyl N-oxide)methyl | H | H | $CH_2CH_2$ | ; |
| 133 | H | H | $CH_3$ | $CH_3CH_2$ | $CH_2CONH-OH$ | H | H | $CH_2CH_2$ | ; |
| 134 | H | H | $CH_3$ | $CH_3CH_2$ | $CH_2CON(CH_3)-OH$ | H | H | $CH_2CH_2$ | ; |
| 135 | H | H | $CH_3$ | $CH_3CH_2$ | $(CH_2)_3COOCH_2CH_3$ | H | H | $CH_2CH_2$ | ; |
| 136 | H | $CH_3$ | H | $CH_3CH_2$ | (4-pyridyl N-oxide)methyl | H | H | $CH_2CH_2$ | ; |
| 137 | H | $CH_3$ | H | $CH_3CH_2$ | (3-pyridyl N-oxide)methyl | H | H | $CH_2CH_2$ | ; |
| 138 | H | H | $CH_3$ | $CH_3CH_2$ | $CH_2CH(CH_3)COOH$ | H | H | $CH_2CH_2$ | ; |
| 139 | H | H | $CH_3$ | $CH_3CH_2$ | $CH_2CH_2C(O)NH$-cyclopropyl | H | H | $CH_2CH_2$ | ; |
| 140 | H | H | $CH_3$ | $CH_3CH_2$ | $CH_2CONHCH_2CH_3$ | H | H | $CH_2CH_2$ | ; |
| 141 | H | H | $CH_3$ | $CH_3CH_2$ | $CH_2CH_2C(O)NH$-(4-pyridyl N-oxide) | H | H | $CH_2CH_2$ | ; |
| 142 | H | H | $CH_3$ | $CH_3CH_2$ | $CH_2CH_2O$-(4-pyridyl) | H | H | $CH_2CH_2$ | ; |
| 143 | H | H | $CH_3$ | $CH_3CH_2$ | $CH_2CH_2O$-(4-pyridyl N-oxide) | H | H | $CH_2CH_2$ | ; |
| 144 | H | $CH_3$ | H | cyclopropyl | (4-pyridyl N-oxide)methyl | H | H | $CH_2CH_2$ | ; |

-continued

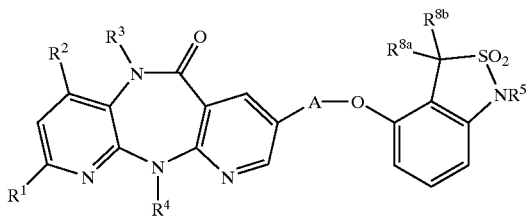

wherein $R^1$, $R^2$, $R^3$, $R^4$ $R^5$, $R^{8a}$, $R^{8b}$, and A are defined as follows:

| Cmpd No. | $R^1$ | $R^2$ | $R^3$ | $R^4$ | $R^5$ | $R^{8a}$ | $R^{8b}$ | A | |
|---|---|---|---|---|---|---|---|---|---|
| 145 | F | CH₃ | H | CH₃CH₂ | (4-pyridyl-N-oxide)CH₂— | H | H | CH₂CH₂ | ; |
| 146 | Cl | CH₃ | H | CH₃CH₂ | (4-pyridyl-N-oxide)CH₂— | H | H | CH₂CH₂ | ; and |
| 147 | Cl | CH₃ | H | CH₃CH₂ | —CH₂C(O)NH-(4-pyridyl-N-oxide) | H | H | CH₂CH₂ | ; |
| 148 | F | H | CH₃ | CH₃CH₂ | (4-pyridyl-N-oxide)CH₂— | H | H | CH₂ | . |

50. The compound according to claim 1, having the following formula:

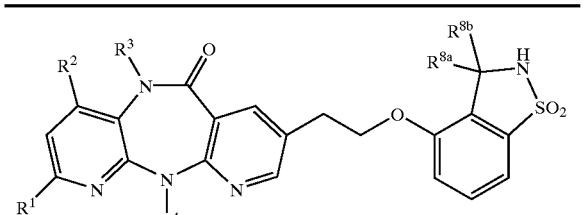

wherein $R^1$, $R^2$, $R^3$, $R^4$, $R^{8a}$, and $R^{8b}$ are defined as follows:

| Cmpd No. | $R^1$ | $R^2$ | $R^3$ | $R^4$ | $R^{8a}$ | $R^{8b}$ | |
|---|---|---|---|---|---|---|---|
| 202 | H | H | CH₃ | CH₃CH₂ | H | H | ; |
| 223 | F | CH₃ | H | CH₃CH₂ | H | H | ; |
| 224 | H | H | CH₃ | CH₃CH₂ | CH₃ | CH₃ | ; and |
| 226 | H | CH₃ | H | cyclopropyl | CH₃ | CH₃ | . |

51. The compound according to claim 1, having the following formula:

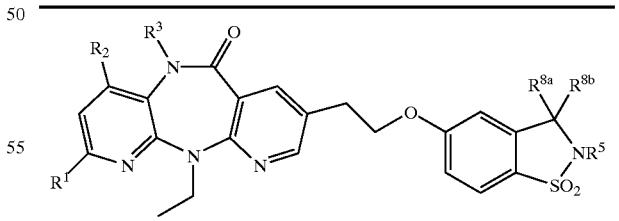

wherein $R^1$, $R^2$, $R^3$, $R^4$ $R^5$, $R^{8a}$, $R^{8b}$ are defined as follows:

| Cmpd No. | $R^1$ | $R^2$ | $R^3$ | $R^5$ | $R^{8A}$ | $R^{8B}$ | |
|---|---|---|---|---|---|---|---|
| 301 | H | H | CH₃ | H | H | H | ; |
| 303 | H | H | CH₃ | CH₃ | H | H | ; |
| 306 | H | H | CH₃ | H | CH₃ | CH₃ | ; |
| 307 | H | H | CH₃ | CH₃ | CH₃ | CH₃ | ; |
| 310 | F | CH₃ | H | H | H | H | ; |

-continued

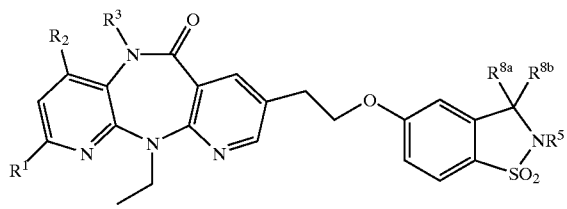

wherein $R^1$, $R^2$, $R^3$, $R^4$ $R^5$, $R^{8a}$, and $R^{8b}$ are defined as follows:

| Cmpd No. | $R^1$ | $R^2$ | $R^3$ | $R^5$ | $R^{8A}$ | $R^{8B}$ | |
|---|---|---|---|---|---|---|---|
| 311 | H | CH$_3$ | H | H | CH$_3$ | CH$_3$ | ; and |
| 325 | F | CH$_3$ | H | H | CH$_3$ | CH$_3$ | . |

52. The compound according to claim 1 having the following formula:

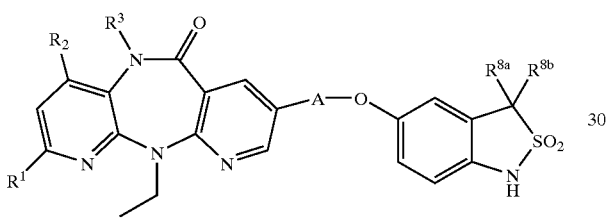

wherein $R^1$, $R^2$, $R^3$, $R^{8a}$, $R^{8b}$, and A are defined as follows:

| Cmpd No. | $R^1$ | $R^2$ | $R^3$ | $R^{8A}$ | $R^{8B}$ | A | |
|---|---|---|---|---|---|---|---|
| 402 | H | H | CH$_3$ | H | H | CH$_2$CH$_2$ | ; |
| 404 | F | H | CH$_3$ | H | H | CH$_2$ | ; and |
| 409 | F | CH$_3$ | H | CH$_3$ | CH$_3$ | CH$_2$CH$_2$ | . |

53. The compound according to claim 1 having the following formula:

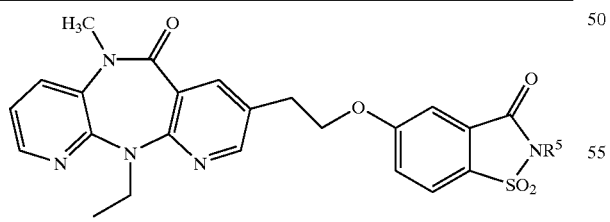

wherein $R^5$ is defined as follows:

| Cmpd No. | $R^5$ | |
|---|---|---|
| 505 | H | ; and |
| 508 | CH$_3$ | . |

54. The compound according to claim 1 having the following formula:

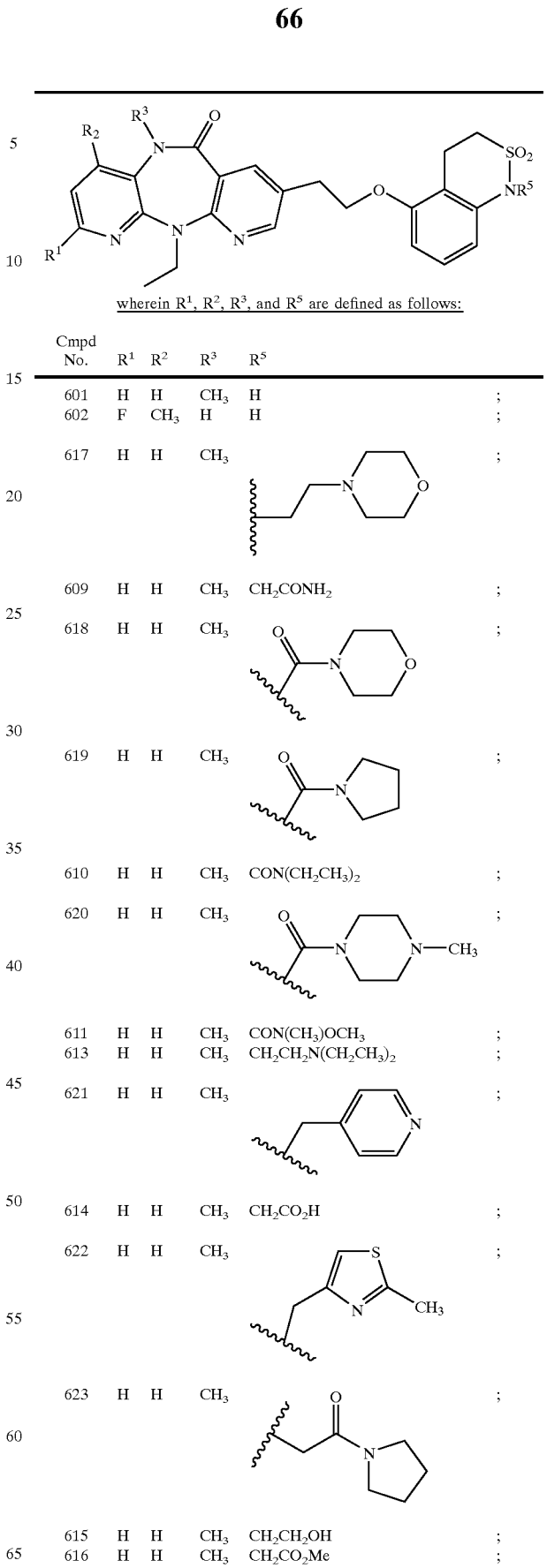

wherein $R^1$, $R^2$, $R^3$, and $R^5$ are defined as follows:

| Cmpd No. | $R^1$ | $R^2$ | $R^3$ | $R^5$ | |
|---|---|---|---|---|---|
| 601 | H | H | CH$_3$ | H | ; |
| 602 | F | CH$_3$ | H | H | ; |
| 617 | H | H | CH$_3$ | (CH$_2$-morpholine) | ; |
| 609 | H | H | CH$_3$ | CH$_2$CONH$_2$ | ; |
| 618 | H | H | CH$_3$ | (C(O)-morpholine) | ; |
| 619 | H | H | CH$_3$ | (C(O)-pyrrolidine) | ; |
| 610 | H | H | CH$_3$ | CON(CH$_2$CH$_3$)$_2$ | ; |
| 620 | H | H | CH$_3$ | (C(O)-N-methylpiperazine) | ; |
| 611 | H | H | CH$_3$ | CON(CH$_3$)OCH$_3$ | ; |
| 613 | H | H | CH$_3$ | CH$_2$CH$_2$N(CH$_2$CH$_3$)$_2$ | ; |
| 621 | H | H | CH$_3$ | (CH$_2$-4-pyridyl) | ; |
| 614 | H | H | CH$_3$ | CH$_2$CO$_2$H | ; |
| 622 | H | H | CH$_3$ | (CH$_2$-2-methylthiazole) | ; |
| 623 | H | H | CH$_3$ | (CH$_2$C(O)-pyrrolidine) | ; |
| 615 | H | H | CH$_3$ | CH$_2$CH$_2$OH | ; |
| 616 | H | H | CH$_3$ | CH$_2$CO$_2$Me | ; |

-continued

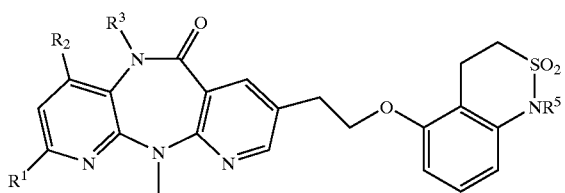

wherein R¹, R², R³, and R⁵ are defined as follows:

| Cmpd No. | R¹ | R² | R³ | R⁵ |
|---|---|---|---|---|
| 624 | H | H | $CH_3$ | (pyridinium N-oxide-CH₂-) ; |
| 625 | H | H | $CH_3$ | $CH_2CH_2CH_2CO_2H$ ; |
| 626 | H | H | $CH_3$ | (tetrazole-CH₂-) ; |
| 627 | H | H | $CH_3$ | $CH_2SO_2CH_3$ ; |
| 628 | H | H | $CH_3$ | $(CH_2)_3COOCH_2CH_3$ ; |
| 629 | H | H | $CH_3$ | (3-pyridyl-CH₂-) ; |
| 630 | H | H | $CH_3$ | $(CH_2)_3SO_2NH_2$ ; |
| 631 | H | H | $CH_3$ | $CH_2CONHSO_2CH_3$ ; |
| 632 | H | H | $CH_3$ | (3-pyridyl N-oxide-CH₂-) ; |
| 633 | H | H | $CH_3$ | $(CH_2)_2SO_3H$ ; |
| 634 | H | H | $CH_3$ | $(CH_2)_2C(CH_2)_2COOH$ ; |
| 635 | H | H | $CH_3$ | $(CH_2)_3CONH_2$ ; |
| 636 | H | H | $CH_3$ | $(CH_2)_3CONHNH_2$ ; |
| 637 | H | H | $CH_3$ | (—CH₂—C(=O)—NH—C(CH₃)₂—COOH) ; |
| 638 | H | H | $CH_3$ | (—CH₂—C(=O)—NH—C(cyclopropyl)—COOH) ; |
| 639 | H | H | $CH_3$ | $CH_2CH_2OCONH_2$ ; |
| 640 | H | H | $CH_3$ | $(CH_2)_3CONHNHCH_2CF_3$ ; |
| 641 | H | H | $CH_3$ | $CH_2CONHC(CH_3)_2CONHNH_2$ ; and |
| 642 | H | H | $CH_3$ | (imidazol-2-yl-CH₂CH₂-) . |

55. The compound according to claim 1 having the following formula:

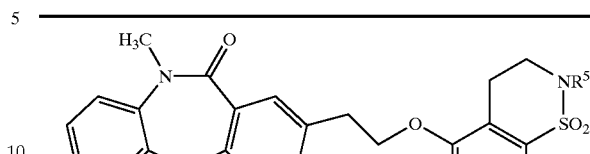

wherein R⁵ is defined as follows:

| Cmpd No. | R⁵ | |
|---|---|---|
| 712 | H | ; |
| 713 | $(CH_2)_3COOH$ | ; and |
| 714 | $(CH_2)_3CONHNH_2$ | . |

56. The compound according to claim 1 having the following formula:

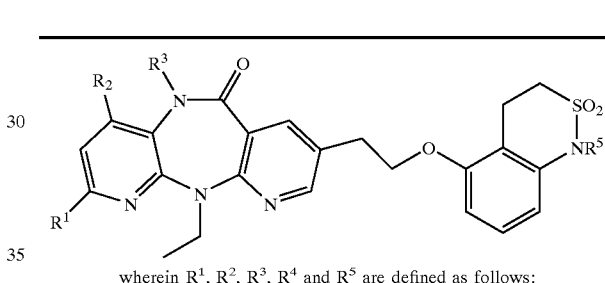

wherein R¹, R², R³, R⁴ and R⁵ are defined as follows:

| Cmpd No. | R¹ | R² | R³ | R⁵ | |
|---|---|---|---|---|---|
| 803 | H | H | $CH_3$ | $CH_3$ | ; |
| 804 | H | $CH_3$ | H | $CH_3$ | ; |
| 805 | H | H | H | $CH_3$ | ; |
| 806 | H | H | $CH_3CH_2$ | $CH_3$ | ; |
| 807 | H | H | $CH_3$ | $CH_2CH_3$ | ; |
| 808 | H | H | $CH_3$ | H | ; and |
| 809 | H | H | $CH_3$ | $(CH_2)_3COOH$ | . |

57. A process for producing a compound of formula I:

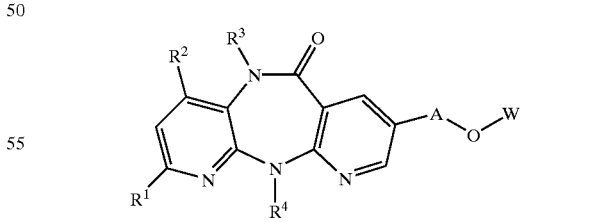

I wherein A, R¹, R², R³, R⁴ and W are as described in claim 1, comprising:

a) removing, in a mixture of an aqueous base or an aqueous acid in a co-solvent, the protecting group (PG) from:

a) coupling a compound of formula 2

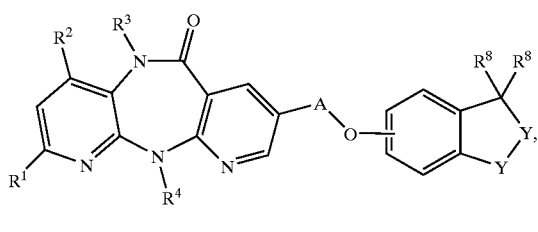

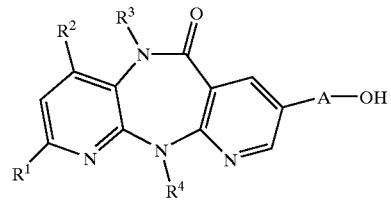

wherein A, $R^1$, $R^2$, $R^3$, and $R^4$ are as described in claim 1, with a compound of the formula

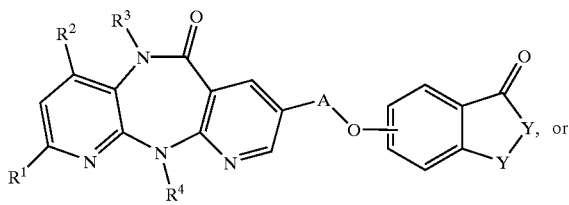

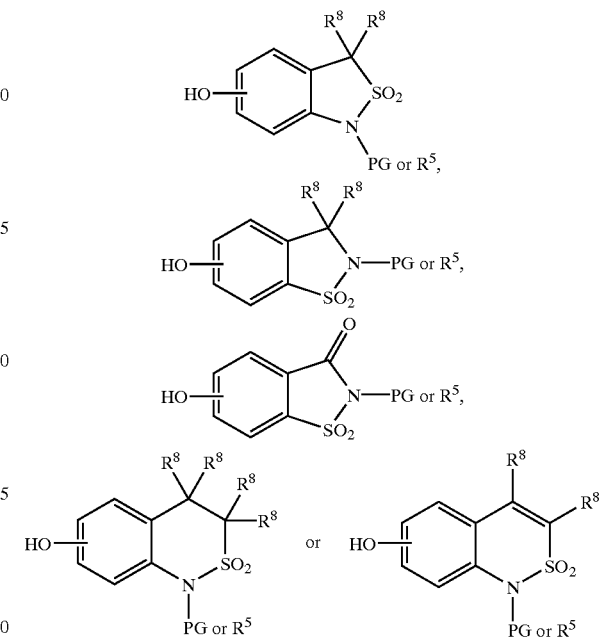

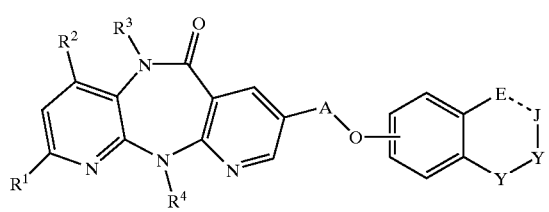

wherein one of Y is $SO_2$ and the other Y is N-PG, wherein PG is a nitrogen protecting group removable under mildly acidic, alkaline or reductive conditions, to produce compounds of formula I, wherein E, J and $R^8$ are as defined in claim 1.

wherein PG is a nitrogen protecting group removable under mildly acidic, alkaline or reductive conditions; and $R^5$ and $R^8$ are as described in claim 1, to produce compounds of formula I when $R^5$ is present;

58. A process, according to claim 57, for producing a compound of formula I, comprising:

b) basifying the product from a).

59. A process, according to claim 58, for producing a compound of formula I, comprising:

c) adding $R^5$-X to the product from step b), wherein $R^5$ is as described in claim 1 and X is a leaving group.

60. A process for producing a compound of formula I:

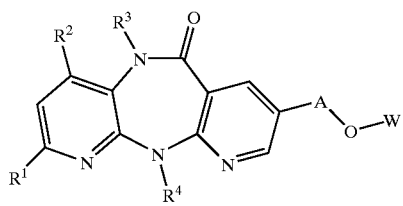

wherein A, $R^1$, $R^2$, $R^3$, $R^4$ and W are as described in claim 1, comprising:

b) or alternatively, when PG is present, removing said PG under mildly acidic, alkaline or reductive conditions;

c) basifying the product from step b); and d) adding $R^5$-X to produce compounds of formula I, wherein $R^5$ is as described in claim 1 and X is a leaving group.

61. A pharmaceutical composition for the treatment of HIV infection, comprising a compound of formula I, as claimed in claim 1, or a pharmaceutically acceptable salt thereof, and a pharmaceutically acceptable carrier.

62. A method for the treatment of HIV infection, comprising administering to a patient an HIV inhibiting amount of a compound of formula I according to claim 1, or a pharmaceutically acceptable salt thereof.

* * * * *